(12) United States Patent
Rothstein et al.

(10) Patent No.: US 8,206,931 B2
(45) Date of Patent: Jun. 26, 2012

(54) METHODS OF IDENTIFYING MODULATORS OF CELLULAR GLYCOSYLATION USING GTRAP3-18

(75) Inventors: Jeffrey D. Rothstein, Catonsville, MD (US); Alicia Ruggiero, Nashville, TN (US)

(73) Assignee: The Johns Hopkins University, Baltimore, MD (US)

( * ) Notice: Subject to any disclaimer, the term of this patent is extended or adjusted under 35 U.S.C. 154(b) by 0 days.

(21) Appl. No.: 10/542,435

(22) PCT Filed: Jan. 18, 2004

(86) PCT No.: PCT/US2004/001162
§ 371 (c)(1),
(2), (4) Date: May 2, 2006

(87) PCT Pub. No.: WO2004/065932
PCT Pub. Date: Aug. 5, 2004

(65) Prior Publication Data
US 2006/0211042 A1    Sep. 21, 2006

Related U.S. Application Data

(60) Provisional application No. 60/440,717, filed on Jan. 17, 2003.

(51) Int. Cl.
*C12P 19/18*    (2006.01)
*G01N 33/53*    (2006.01)
*G01N 33/567*   (2006.01)
*A61K 48/00*    (2006.01)

(52) U.S. Cl. ............ 435/6.17; 435/7.21; 435/7.95; 435/97

(58) Field of Classification Search .............. None
See application file for complete search history.

(56) References Cited

U.S. PATENT DOCUMENTS
6,808,893 B1 * 10/2004 Rothstein et al. ............ 435/69.1

FOREIGN PATENT DOCUMENTS
| WO | WO/01/30968 A2 | 5/2001 |
| WO | WO/01/30968 A3 | 5/2001 |
| WO | WO 0130968 A2 * | 5/2001 |

OTHER PUBLICATIONS

Butchbach MER, Guo H, Lin C-L G. Methyl-β-cyclodextrin but not retinoic acid reduces EAAT3-mediated glutamate uptake and increases GTRAP3-18 expression. Journal of Neurochemistry, 84:891-894. (2003).*

Ikemoto MJ, Inoue K, Akiduki S, Osugi T, Imamura T, Ishida N, Ohtomi M. Identification of addicsin/GTRAP3-18 as a chronic morphine-augmented gene in amygdala. Neuroreport 13(16):2079-2084. Nov. 15, 2002.*

Butchbach et al. Journal of Neurochemistry 84: 891-894, Feb. 15, 2003.*

Sáez-Valero et al. Journal of Neurology, Neurosurgery and Psychiatry, 69: 664-667, 2000.*

Fassbender et al. Proc. Natl. Acad. Sci. U.S.A. 98, 5856-5861, 2001.*

Lin et al. Nature 410: 84-88, published Mar. 1, 2001.*

Hirabayashi and Kasai, Journal of Chromatography B 771: 67-87, May 5, 2002.*

Trotti et al. Journal of Biological Chemistry, 276(1): 576-582, 2001.*

Wahle et al., J Cell Biol, 135(6):1876-1877, Dec. 15, 1996.*

Ikemoto, M.J. et al., "Identification of addicsin/GTRAP3-18 as a chronic morphine-augmented gene in amygdala", *Molecular Neuroscience*, vol. 13, No. 16, pp. 2079-2084, 2002.

Jackson, Mandy et al, "Modulation of the neuronal glutamate transporter EAAT4 by two interacting proteins", *Nature*, vol. 410, pp. 89-93, 2001.

Butchbach et al., "The Effect of Methyl-Beta-Cyclodextrin on the Expression and Function of the Eaat3-Interacting Protein Gtrap3-18", *Society for Neuroscience Abstract Viewer and Itinerary Planner*, vol. 2002, 2002, 2 pages, Abstract No. 441.7, URL-http://sf, XP001538959 & 32nd Annual Meeting of the Society for Neuroscience; Orlando, Florida, USA; Nov. 2-7, 2002.

Ruggiero et al., "Gtrap3—18: A General Regulator of Eaat Activity and Pngase F Sensitive Glycosylation", *Society for Neuroscience Abstract Viewer and Itinerary Planner*, vol. 2002, 2002, 1 page, Abstract No. 441.11, URL-http://sf, XP001538958 & 32nd Annual Meeting of the Society for Neuroscience; Orlando, Florida, USA; Nov. 2-7, 2002.

Maragakis and Rothstein, "Glutamate transporters: animal models to neurologic disease," Neurobiol Dis., (3):461-73 (2004).

Watabe et al., "A dominant role of GTRAP3-18 in neuronal glutathione synthesis," J Neurosci., 28(38):9404-13 (2008).

* cited by examiner

*Primary Examiner* — Daniel E Kolker
*Assistant Examiner* — Stacey MacFarlane
(74) *Attorney, Agent, or Firm* — DLA Piper LLP (US)

(57) ABSTRACT

The present invention provides methods and compositions for identifying compounds which modulate cellular glycosylation. The invention further provides methods for treating subjects suffering from or at risk of developing a glycosylation associated disorder.

8 Claims, 7 Drawing Sheets

```
  1 ATGGACGTGAACCTTGCCCCGCTCCGTGCCTGGGATGATTTCTTCCCGGGCTCTGATCGTTTCGCACGGCCGGACTTCAGGGATATATCC
    M  D  V  N  L  A  P  L  R  A  W  D  D  F  F  P  G  S  D  R  F  A  R  P  D  F  R  D  I  S
                                                          _____
                                                                          1
 91 AAATGGAACAACCGTGTAGTGAGCAATCTGCTCTATTACCAGACCAACTACCTGGTGGTGGCTGCCATGATGATTTCAGTCGTTGGGTTT
    K  W  N  R  V  V  S  N  L  L  Y  Y  Q  T  N  Y  L  V  V  A  A  M  M  I  S  V  V  G  F
                                           _____
                                                         2
181 CTGAGCCCCTTCAACATGATCCTTGGAGGAATCATTGTGGTGCTGGTGTTCACGGGGTTTGTGTGGGCAGCACACAATAAAGACATCCTC
    L  S  P  F  N  M  I  L  G  G  I  I  V  V  L  V  F  T  G  F  V  W  A  A  H  N  K  D  I  L
                                _____
                                                       3
271 CGCCGGATGAAGAAGCAGTACCCAACGGCCTTTGTCATGGTGGTCATGCTAGCCAGCTACTTCCTCATATCCATGTTTGGGGGTGTCATG
    R  R  M  K  K  Q  Y  P  T  A  F  V  M  V  V  M  L  A  S  Y  F  L  I  S  M  F  G  G  V  M
                                                     _____
                                                                  4
361 GTCTTTGTGTTTGGCATCACGTTTCCCTTATTGTTGATGTTCATCCATGCATCCCTGAGACTTCGAAACCTCAAGAACAAACTGGAAAAT
    V  F  V  F  G  I  T  F  P  L  L  L  M  F  I  H  A  S  L  R  L  R  N  L  K  N  K  L  E  N
                                                        _____
451 AAAATGGAGGGAATAGGCTTGAAGAAAACGCCGATGGGCATCATCCTGGATGCCTTGGAACAGCAGGAAGACAGCATCAATAAATTTGCT
    K  M  E  G  I  G  L  K  K  T  P  M  G  I  I  L  D  A  L  E  Q  Q  E  D  S  I  N  K  F  A
541 GACTACATCAGCAAAGCCAGGGAGTAA
    D  Y  I  S  K  A  R  E  *
```

Supplement 1. Nucleotide and amino acid sequence of GTRAP3-18. Lines 1-4: putative transmembrane domains, double lines: potential protein kinase-dependent phosphorylation sites (S/T-X-K/R). GenBank accession number for GTRAP3-18 is AF240182.

Fig. 1

METHODS OF IDENTIFYING MODULATORS OF CELLULAR GLYCOSYLATION USING GTRAP3-18

CROSS REFERENCE TO RELATED APPLICATIONS

This application is a 35 USC §371 National Stage application of PCT Application No. PCT/US2004/001162 filed Jan. 18, 2004; which claims the benefit under 35 USC §119(e) to U.S. Application Ser. No. 60/440,717 filed Jan. 17, 2003, now abandoned. The disclosure of each of the prior applications is considered part of and is incorporated by reference in the disclosure of this application.

GOVERNMENT SUPPORT

This work described herein was supported by a grant from the National Institutes of Health (Grant No. RO1—NS40151). Therefore, the U.S. Government may have certain rights in the invention.

BACKGROUND OF THE INVENTION

1. Field of the Invention

The present invention features screening assays for identifying modulators of cellular glycosylation. Further provided are methods for treating subjects suffering from or at risk of developing glycosylation associated disorders, particularly neurological disorders.

2. Background

Neurological disorders can significantly impact the central nervous system (CNS) and motor neuron units. For example, certain neurological disorders of the CNS are known to adversely affect the brain and associated structures. Neurological disorders affecting motor neuron units have been grouped into motor neuron diseases and peripheral neuropathies. See generally Kandel, E. R. et al; (1991) in *Principles of Neuroscience*, Appleton & Lange, Norwalk, Conn.; and Rowland, L. P. (ed.) (1982) in *Human Motor Neuron Diseases*. New York. Raven Press.

An illustrative motor neuron disease is amyotrophic lateral sclerosis (ALS). ALS has been reported to be a chronic neuromuscular disorder having recognized clinical manifestations. For example, it has been suggested that degeneration of cortical and spinal/bulbar motor neurons may play a key role in the disorder. ALS is nearly always fatal. About 95% of all ALS cases are sporadic, with many of the remaining cases showing autosomal dominant inheritance. See e.g., Kuncl R. W. et al., (1992) *Motor Neuron Diseases In Diseases of the Nervous System*, Asbury et al. eds. (Philadelphia W.B. Saunders) pp. 1179-1208; Brown, R. H., (1996) *Amer. Neurol.* 30:145; Siddique, T. and Deng., H. X. (1996) *Hum. Mol. Genetics* 5:1465).

Specific CNS disorders have been also described. In particular, some have been attributed to cholinergic, dopaminergic, adrenergic, serotonergic deficiencies or combinations thereof. CNS disorders of severe impact include pre-senile dementia (sometimes referred to as Alzheimer's disease (AD) or early-onset Alzheimer's disease), senile dementia (dementia of the Alzheimer's type), Parkinson's disease (PD), and Huntington's disease (HD, sometimes referenced as Huntington's chorea). Such CNS disorders are well-represented in the human population. See generally; Gusella, J. F. et al. (1983) *Nature* 306: 234; Borlauer. W. and Jprmuloewoca. P. (eds.) (1976); *Adv. in Parkinsonism: Biochemistry, Physiology, Treatment. Fifth International Symposium on Parkinson's Disease* (Vienna) Basel: Roche; and references cited therein.

Significant attention has been directed towards understanding the etiology of motor neuron diseases. For example, abnormal levels of certain excitotoxic neurotransmitters have been reported to adversely contribute to many motor neuron diseases. In particular, glutamate-mediated excitotoxicity is recognized to have a critical role in ALS. See e.g., Rothstein J. D. et al., (1990) Ann. Neurol. 28: 18; Rothstein J. D. et al. (1992) *N. Engl. Med.* 326: 1464; Rothstein J. D. et al. (1993) *PNAS (USA)* 90: 6591; and Lacomblez, L. et al., (1996) *Lancet* 347: 1179.

There has been substantial efforts towards understanding mechanisms for reducing glutamate levels in the nervous system. For example, high-affinity, sodium-dependent glutamate transport is one reported means of inactivating glutamate.

There have been attempts to treat or prevent neurological disorders of the CNS and the motor neuron units. However, most existing therapies do not always stem the development or severity of the disorders in afflicted patients. See e.g., Rowell, (1987) *Adv. Behav. Biol.* 31: 191; Rinne, et al. *Brain Res*. (1991) 54: 167; U.S. Pat. No. 5,210,076 to Berliner; Yurek, D. M. (1990) *Ann. Rev. Neurosci.* 13: 415, and Rowland et al. supra.

The Na+-dependent glutamate transporter sub-family rapidly reduces glutamate levels around the synaptic cleft and is critical for preserving nervous system function. They are named excitatory amino acid transporters (EAAT). Two of the five gene products are expressed in astrocytes and glial supportive cells in the CNS, GLT-1/EAAT2 and GLAST/EAAT1. Their predominant functions have been postulated to be protection against excitotoxicity, and the recycling of a neuronal transmitter pool of glutamate. The Na+-dependent glutamate transporter EAAT4 is found in Purkinje cells of the cerebellum, and EAAT5 is restricted to the retina. The general neuronal transporter is EAAC1/EAAT3, the predominant high affinity Na+-dependent glutamate transporter in cortical neurons. This transporter is found in diverse neuronal populations, including the cortex, hippocampus, and cerebellum.

Given the involvement of glutamate transporters in nervous system function, there exists a need in the art for therapies which can modulate glutamate transporter activity. Furthermore, because glutamate transporters are modified by glycosylation, there exists a need in the art for therapies which can modulate glutamate transporter activity via modulation of glutamate transporter glycosylation.

SUMMARY OF THE INVENTION

The present invention is based, at least in part, on the discovery that the glutamate transporter regulatory protein GTRAP3-18 acts as a general regulator of cellular glycosylation, including glycosylation of neurotransmitter transporters and receptors, including glutamate transporters, dopamine transporters, GABA transporters, and amino acid transporters (ASCTs). Accordingly, the present invention provides methods for the identification of compounds useful in modulating cellular glycosylation as well as methods for the diagnosis and treatment of disorders or diseases associated with glycosylation, including but not limited to neurological disorders.

In one aspect, the invention provides methods for identifying a compound capable of modulating glycosylation. The methods include contacting a cell expressing a GTRAP3-18 nucleic acid or polypeptide (e.g., a neuronal cell) with a test compound and assaying the ability of the test compound to modulate the expression of a GTRAP3-18 nucleic acid or the activity of a GTRAP3-18 polypeptide.

In another aspect, the invention provides methods for identifying a compound capable of treating a glycosylation associated disorder, e.g., a neurological disorder. The methods include assaying the ability of the compound to modulate GTRAP3-18 nucleic acid expression or GTRAP3-18 polypeptide activity. In one embodiment, the ability of the compound to modulate nucleic acid expression or GTRAP3-18 polypeptide activity is determined by detecting glycosylation of cellular proteins, e.g., GTRAP3-18 target molecules. In another embodiment, the ability of the compound to modulate nucleic acid expression or GTRAP3-18 polypeptide activity is determined by detecting modulation of glutamate transport in a cell.

In a further aspect, the invention features a method for modulating glycosylation. The method includes contacting a cell (e.g., a neuronal cell) with a GTRAP3-18 modulator.

In yet another aspect, the invention features a method for treating a subject having a glycosylation associated disorder (e.g., a disorder characterized by aberrant GTRAP3-18 polypeptide activity or aberrant GTRAP3-18 nucleic acid expression, such as a neurological disorder). The method includes administering to the subject a GTRAP3-18 modulator, e.g., in a pharmaceutically acceptable formulation or by using a gene therapy vector. In one embodiment, the GTRAP3-18 modulator may be a small molecule, an anti-GTRAP3-18 antibody, a GTRAP3-18 polypeptide comprising the amino acid sequence of SEQ ID NO:2, or a fragment thereof, a GTRAP3-18 polypeptide comprising an amino acid sequence which is at least 90 percent identical to the amino acid sequence of SEQ ID NO:2, an isolated naturally occurring allelic variant of a polypeptide consisting of the amino acid sequence of SEQ ID NO:2, an antisense GTRAP3-18 nucleic acid molecule, a nucleic acid molecule of SEQ ID NO:1, or a fragment thereof, or a ribozyme.

In another aspect, the invention provides a method for modulating, e.g., increasing or decreasing, glycosylation in a subject by administering to the subject a GTRAP3-18 modulator.

Other features and advantages of the invention will be apparent from the following detailed description and claims.

BRIEF DESCRIPTION OF THE DRAWINGS

FIG. 1 depicts the nucleotide (SEQ ID NO:1) and amino acid (SEQ ID NO:2) sequences of GTRAP-18 (GenBank Accession No. AF240182). The underlined sequences (numbered 1-4) represent putative transmembrane domains. The double-underlined sequences represent potential protein kinase-dependent phosphorylation sites (consensus sequence: [S/T]-X-[K/R]).

FIGS. 4A and 4B: Co-transfection of rEAAT3/EAAC1 and GTRAP3-18 in HEK 293T cells at equal transfection ratio reduces EAAC1 $Na^+$-dependent L[$^3$H]-glutamate uptake by approximately 20%, following background correction for the cell line. The decrease in transport can be brought to a higher percent of control EAAC1 expression by increasing the transfection ratios of EAAC1 to GTRAP3-18 cDNA. Co-transfection of rEAAT4 and GTRAP3-18 had a similar effect on transport. FIGS. 4C and 4D: Expansion of the analysis to the glial transporters rEAAT1 and rEAAT2 also showed a significant decrease in $Na^+$-dependent L-[$^3$H]-glutamate uptake glutamate uptake following transfection in HEK 293T cells. These transporters have a higher basal uptake activity and were measured at 40 µM total glutamate. Data are the mean±SEM of at least four independent observations and were compared by students t test (** $p<0.005$), and error bars are shown.

FIG. 6A: HEK 293T cells were transfected either with EAAC1 or EAAC1 and GTRAP3-18. The cells were harvested after 48 hours and labeled with biotin. The cell lysates were prepared as duplicate samples and incubated for 12 hours with or without the addition of the de-glycosylating enzymes PNGase F and/or Endo H. The supernatant was incubated with immobilized monomeric avidin beads to isolate biotin labeled proteins. Western blots were incubated with C-EAAC1 polyclonal and actin monoclonal antibodies as a marker for intracellular contamination of the membrane fraction. Expression of GTRAP3-18 was visualized with HA monoclonal antibody. Comparison of the effect of digestion with PNGase F and Endo H to the effect of GTRAP3-18 co-expression with EAAC1 indicates that the result is the same reproducible shift in Western immunoreactivity. Digestion of co-expressed lysates did not induce any further change in the apparent molecular weight of EAAC1.

This data implicates GTRAP3-18 as a modulator of EAAC1 glycosylation. This experiment was also repeated for the other EAATs. FIG. 6B: Transporter N-linked oligosaccharides are processed to completion in the golgi to form complex oligosaccharides. Therefore, they cannot be cleaved with the high mannose specific endoglycosidase H. The molecular weight of PNGase F cleaved transporter is the same as GTRAP3-18 co-expressed transporter.

DETAILED DESCRIPTION OF THE INVENTION

Figure 2:
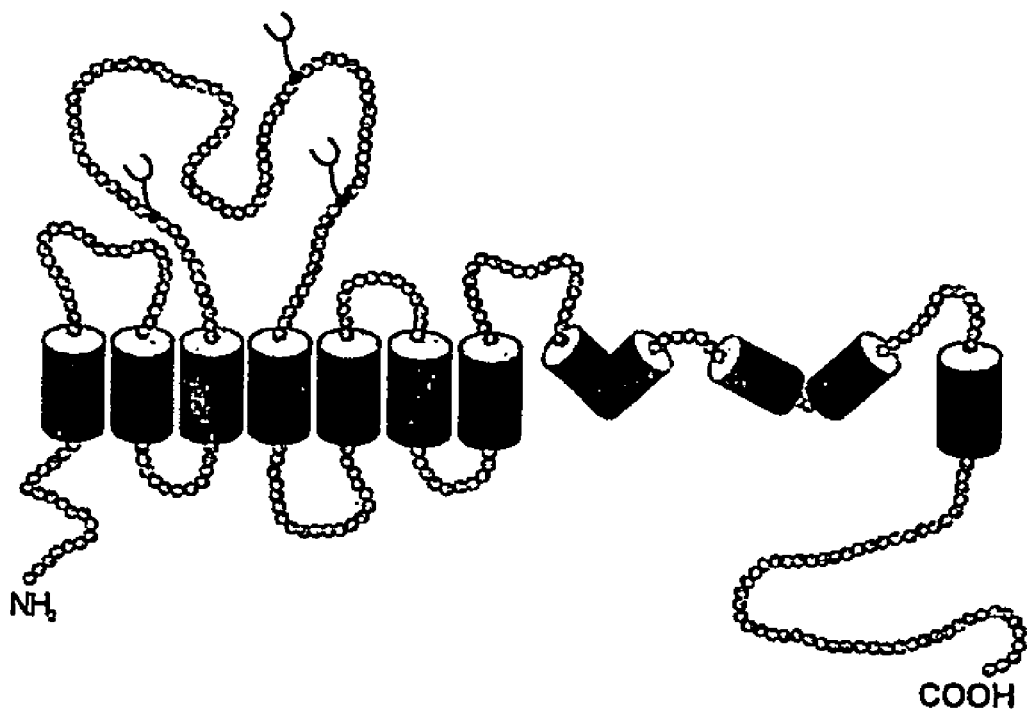
FIG. 2 depicts a topology model of rEAAT3 based on solvent accessible amino acid residue studies on EAAT1 (Seal, R. P. et al. (2000) Neuron 25:695-706). Reentrant loop domains are located under the bracket.
Figure 3:
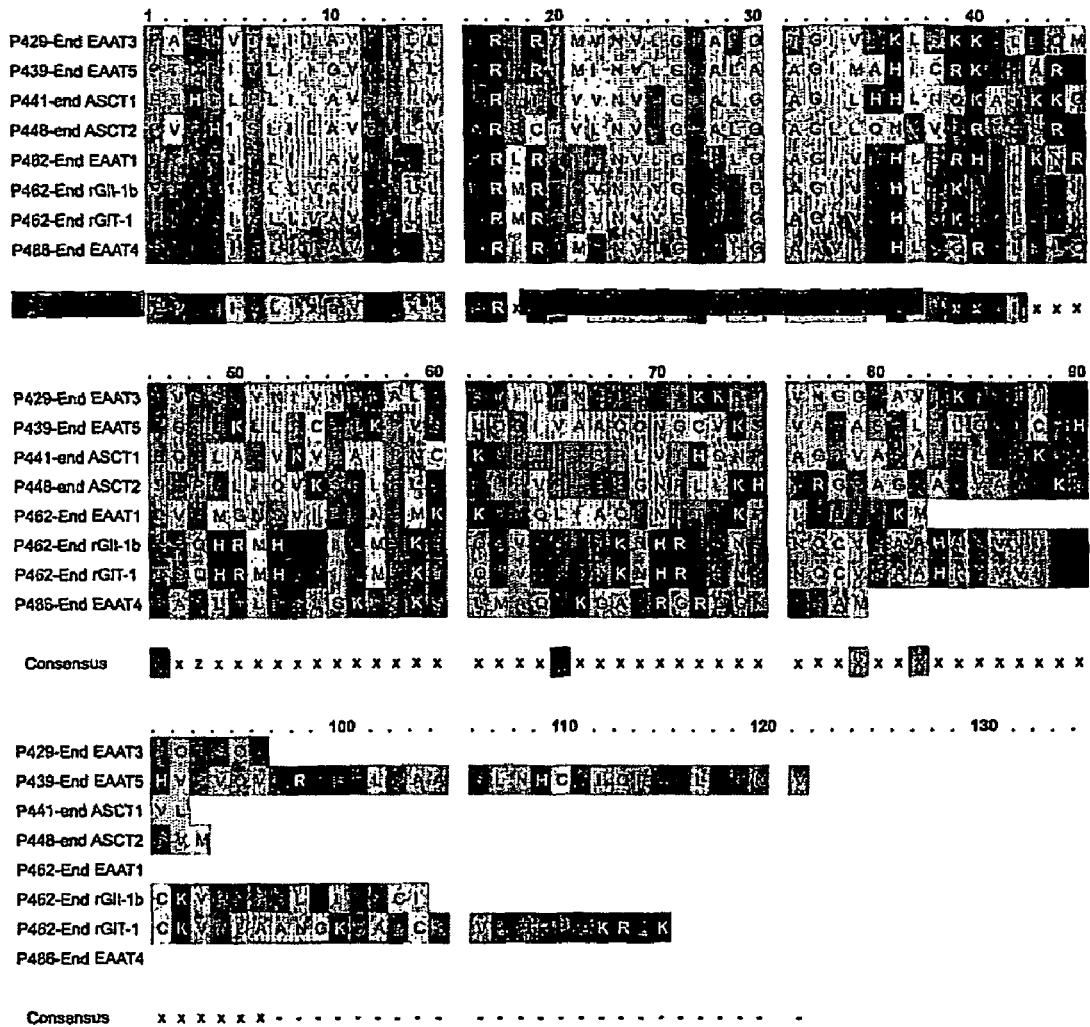
FIG. 3 depicts an amino acid alignment of the C-terminal sequences of EAATs (Excitatory Amino Acid Transporters) and ASCT (Adenine Serine Cysteine Transporter) isoforms. ASCT is the closest related protein family to the EAAT. This alignment highlights the conservation of sequence through the final reentrant (RL3) and extracellular loops and final transmembrane domain (TM8) and the divergence following through the cytoplasmic region. This amino acid sequence for rEAAT3 was used as bait for the yeast-two-hybrid screen that lead to the cloning of GTRAP3-18. The final extracellular loop may be the interaction site for GTRAP3-18 and the EAAT within the endoplasmic reticulum. The sequences depicted are as follows: P429-End EAAT3: SEQ ID NO:3; P439-End EAAT5: SEQ ID NO:4; P441-end ASCT1: SEQ ID NO:5; P448-end ASCT2: SEQ ID NO:6; P462-End EAAT1: SEQ ID NO:7; P462-End rGlt-1b: SEQ ID NO:8; P462-End rGlT-1: SEQ ID NO:9; P486-End EAAT4: SEQ ID NO:10.

The present invention is based, at least in part, on the discovery that co-expression of GTRAP3-18 with glutamate transporters results in decreased glycosylation of the transporters, as well as a decrease in glutamate transporter activity, as measured by cellular glutamate uptake. The present invention is further based, at least in part, on the discovery that GTRAP3-18 acts as a general regulator of cellular glycosylation. Accordingly, the present invention provides methods for the identification of compounds useful in modulating cellular glycosylation as well as methods for the diagnosis and treatment of disorders or diseases associated with glycosylation, including but not limited to neurological disorders.

GTRAP3-18 (Glutamate Transporter Associated Protein of EAAT3) is a 22 kD protein originally isolated from a rat brain cDNA library through yeast-two-hybrid screen using the C-terminal portion of rEAAT3/EAAC1 (Lin, C.-I. et al. (2001) Nature 410:84-88; International Publication No. WO 01/30968). GTRAP3-18 has a physiologic effect on rEAAT3 activity and decreases its affinity for the substrate glutamate as determined by kinetic analysis. The data presented herein show he mechanism of this effect on transporter activity is linked to alterations in the glycosylation state of the transporter. The EAAT family contain conserved N-linked glycosylation consensus sequences and are processed in the golgi to have complex N-linked oligosaccharides on the mature EAAT protein. This complex oligosaccharide may be cleaved in vitro through digestion with an endoglycosidase, endoglycosidae F (PNGase F). Incubation of rEAAT3 (wherein the "r" refers to "rat"), rEAAT4, rEAAT1, and rEAAT2 transfected HEK 293 cell lysates with PNGase F endoglycosidase results in a decrease in the electro-mobility of these proteins by 10 kD. Following co-expression with GTRAP3-18, the EAAT family members tested also were observed to have a decreased electro-mobility. This change is reproducible and creates a protein with the same apparent molecular weight obtained following PNGase F digest. The electro-mobility of co-expressed transporters with GTRAP3-18 can not be decreased further through PNGase F digestion. Co-expression of GTRAP3-18 with the EAAT family members significantly decreases their activity as measured by sodium dependent $^3$H-L-glutamate uptake. The data suggest that the decrease in electro-mobility, resulting from the loss of N-linked oligosaccharides, is responsible for the measured decrease in activity. The amino acid sequence used in the original yeast-two-hybrid screen where GTRAP3-18 was identified corresponds to the final extracellular loop of EAAT.

Immunofluorescence and co-localization data show that GTRAP3-18 is a reticular protein that interacts with the extracellular loop of the EAATs when they are nascent chains in the endoplasmic reticulum. GTRAP3-18 appears to alter the glycosylation profile of the EAAT through this endoplasmic reticulum association. All of the above data suggest that GTRAP3-18 is a general regulator of cellular glycosylation.

The acidic amino acids glutamate (Glu) and aspartate are the predominant excitatory neurotransmitters in the mammalian central nervous system (CNS). Although there are millimolar concentrations of these excitatory amino acids (EAAs) in the brain, extracellular concentrations are maintained in the low micromolar range to facilitate crisp synaptic transmission and to limit the neurotoxic potential of these EAAs. A family of $Na^+$-dependent high affinity transporters is responsible for the regulation and clearance of extracellular EAAs.

Glutamate and aspartate activate ligand-gated ion channels that are named for the agonists N-methyl-D-aspartate (NMDA), a-amino-3-hydroxy-5-methyl-4-isoxazolepropionate (AMPA), and kainate. These ionotropic EAA receptors mediate rapid synaptic depolarization and are important for a number of other physiological processes, including synaptic plasticity and synapse development. The EAAs also activate a family of metabotropic receptors coupled through G-proteins to second messenger systems or ion channels. It is well established that the EAAs are extremely important for normal brain function. However, there is substantial evidence that an extracellular accumulation of EAAs and excessive activation of EAA receptors also contributes to the neuronal cell death observed in acute insults to the CNS. The process known as, 'excitotoxicity', may also contribute to neuronal loss observed in chronic neurodegenerative diseases, including amyotrophic lateral sclerosis (ALS).

The intracellular concentrations of glutamate (5-10 mM) and aspartate (1-5 mM) are 1000-fold to 10,000-fold greater than the extracellular concentrations (<1-10 μM). Unlike many other neurotransmitters, there is no evidence that glutamate or aspartate is metabolized extracellularly. Instead, they are cleared from the extracellular space by transport into neurons and astrocytes.

Several subtypes of $Na^+$-dependent glutamate transporters have been identified through pharmacological strategies and cDNA cloning. Five known distinct cDNA clones that express $Na^+$-dependent high-affinity glutamate transport are referred to herein as GLT-1/EAAT2, EAAC1/EAAT3, GLAST/EAAT1, EAAT4, and EAAT5. There is also evidence for additional heterogeneity of GLT-1 and GLAST that originates from alternate mRNA splicing.

Expression of two of these transporters, GLT-1 and GLAST, is generally restricted to astroglia. Expression of two other transporters, EAAC1 and EAAT4, is generally restricted to neurons, and EAAT5 is thought to be restricted to retina Of the three transporters found in forebrain (GLT-1, GLAST, and EAAC1), GLT-1 appears to be the only transporter that is specific to brain tissue, suggesting that GLT-1 expression is controlled by brain specific mechanisms.

Previously, it was thought that presynaptic transporters had a major role in the clearance of EAAs during synaptic transmission. This was based on the evidence that activity is enriched 2-fold in synaptosomal membrane preparations compared to fractions enriched in mitochondria or myelin. However, it is now known that these membrane preparations contain resealed glial membranes and tremendous amounts of GLT-1 protein. In addition, it has long been known that lesions of specific afferents result in a decrease in $Na^+$-dependent transport in target areas. For example, lesions of the cortical projections to the striatum result in decreased uptake in striatal synaptosomes. These types of studies suggested that there was significant transport into presynaptic terminals, but more recent studies have suggested that these lesions reduce expression of the glial transporters.

Evidence from several complementary strategies strongly suggests that GLT-1 mediates the bulk of $Na^+$-dependent transport of EAAs in the CNS. For example, the pharmacological properties of GLT-1 parallel the predominant component of activity observed in rat brain membranes. Based on the enrichment required to purify GLT-1 to homogeneity, it is thought that GLT-1 represents approximately 1% of total brain protein. Selective immunoprecipitation of GLT-1 from solubilized forebrain tissue and reconstitution of the remaining protein in liposomes, suggests that GLT-1 mediates 90% of transport activity. Anti-sense knock-down of GLT-1 results in the dramatic reductions in synaptosomal transporter activity in several forebrain regions.

Synaptosomal uptake in mice genetically deleted of GLT-1 is 5% of normal. Finally, electrophysiological recording of transporter mediated currents in brain preparations strongly suggest that GLT-1 has a primary role for the clearance of glutamate during synaptic transmission in several forebrain regions.

The expression of GLT-1/EAAT2 is dynamically regulated both in vivo and in vitro. Although GLT-1 is the predominant transporter in the adult CNS, expression is rather low early in development and increases during synaptogenesis in both rats and humans. As described above, lesions of projections to a particular target nucleus results in decreased expression of both glial transporters, GLT-1 and GLAST. These data suggest that the presence of neurons induces and/or maintains expression of the glial transporters.

Several different groups have demonstrated decreased expression of GLT-1 and/or GLAST in animal models of acute insults to the CNS, including stroke and traumatic brain injury. A loss in GLT-1 expression has been demonstrated in patients with ALS. Furthermore, there is evidence of decreased expression of these transporters in humans with chronic neurodegenerative diseases, including Alzheimer's Disease, and Huntington's Disease. Loss of GLT-1 is also a feature of the fatal brain tumor, glioblastoma multiforma.

The GTRAP3-18 modulators identified according to the methods of the invention can be used to modulate glycosylation (e.g., glycosylation of EAAT proteins) and are, therefore, useful in treating or diagnosing glycosylation-associated disorders, e.g., neurological disorders. For example, inhibition of the activity of a GTRAP3-18 molecule can cause increased glycosylation in a subject. Thus, the GTRAP3-18 modulators used in the methods of the invention can be used to treat disorders characterized by insufficient glycosylation, or where increased glycosylation would be desirable. Alternatively, GTRAP3-18 modulators can decrease glycosylation by increasing GTRAP3-18 in the subject. Thus, GTRAP3-18 modulators are also useful in the treatment of disorders characterized by excessive glycosylation, or where decreased glycosylation would be desirable.

As used herein, a "glycosylation associated disorder" includes a disease, disorder, or condition which is associated with abnormal or aberrant glycosylation. Glycosylation associated disorders also include a disease, disorder, or condition associated where modulation of cellular glycosylation would be desirable in a subject. Glycosylation associated disorders can be characterized by a misregulation (e.g., downregulation or upregulation) of GTRAP3-18 activity. Examples of glycosylation associated disorders include CNS and non-CNS disorders that rely on protein glycosylation, including acute neurological disorders such as epilepsy, stroke, traumatic injury, chronic neurological disorders such as Alzheimer's disease, amyotrophic lateral sclerosis, Parkinson's disease, Huntington's disease, spinocerebellar ataxia, general neuromuscular disorders involving acute and chronic nerve or muscle injury, CNS inflammation, and psychiatric disorders such as schizophrenia. Further examples of glycosylation associated disorders include cancer, renal disease, ADS, and inflammatory disorders such as arthritis.

As used interchangeably herein, "GTRAP3-18 activity," "biological activity of GTRAP3-18" or "functional activity of GTRAP3-18," includes an activity exerted by a GTRAP3-18 protein, polypeptide or nucleic acid molecule on a GTRAP3-18 responsive cell or tissue (e.g., a neuron) or on a GTRAP3-18 protein substrate (e.g., an EAAT), as determined in vivo, or in vitro, according to standard techniques. GTRAP3-18 activity can be a direct activity, such as an association with a GTRAP3-18-target molecule. As used herein, a "substrate" or "target molecule" or "binding partner" is a molecule with which a GTRAP3-18 protein binds or interacts in nature, such that GTRAP3-18-mediated function, e.g., modulation of glycosylation, is achieved. A GTRAP3-18 target molecule can be a non-polypeptide molecule (e.g., an oligosaccharide), or a protein or polypeptide (e.g., an EAAT). Examples of such target molecules include proteins in the same signaling path as the GTRAP3-18 protein, e.g., proteins which may function upstream (including both stimulators and inhibitors of activity) or downstream of the GTRAP3-18 protein in a pathway involving regulation of glycosylation. Alternatively, a GTRAP3-18 activity is an indirect activity, such as a cellular signaling activity mediated by interaction of the GTRAP3-18 protein with a GTRAP3-18 target molecule. The biological activities of GTRAP3-18 are described herein. For example, the GTRAP3-18 proteins can have one or more of the following activities: 1) they modulate glycosylation of proteins e.g., cytoplasmic, membrane, and/or extracellular matrix proteins); 2) they modulate the activity of glycosylated proteins; 3) they modulate the activity of EAATs and/or other neurotransmitter transporters (e.g., GAT/GABA transporters, dopamine transporters); 4) the modulate the activity of amino acid transporters (e.g., ASCTs); and/or 5) they modulate glutamate, GABA, dopamine and/or general amino acid transport.

Various aspects of the invention are described in further detail in the following subsections:

I. Screening Assays:

The invention provides methods (also referred to herein as "screening assays") for identifying modulators, i.e., candidate or test compounds or agents (e.g., peptides, peptidomimetics, small molecules, ribozymes, or GTRAP3-18 antisense molecules) which bind to GTRAP3-18 proteins, have a stimulatory or inhibitory effect on GTRAP3-18 expression or GTRAP3-18 activity, or have a stimulatory or inhibitory effect on the expression or activity of a GTRAP3-18 target molecule. Compounds identified using the assays described herein may be useful for treating glycosylation associated disorders.

Candidate/test compounds include, for example, 1) peptides such as soluble peptides, including Ig-tailed fusion peptides and members of random peptide libraries (see, e.g., Lam, K. S. et al. (1991) Nature 354:82-84; Houghten, R. et al. (1991) Nature 354:84-86) and combinatorial chemistry-derived molecular libraries made of D- and/or L-configuration amino acids; 2) phosphopeptides (e.g., members of random and partially degenerate, directed phosphopeptide libraries, see, e.g., Songyang, Z. et al. (1993) Cell 72:767-778); 3) antibodies (e.g., polyclonal, monoclonal, humanized, anti-idiotypic, chimeric, and single chain antibodies as well as Fab, F(ab').sub.2, Fab expression library fragments, and epitope-binding fragments of antibodies); and 4) small organic and inorganic molecules (e.g., molecules obtained from combinatorial and natural product libraries).

The test compounds of the present invention can be obtained using any of the numerous approaches in combinatorial library methods known in the art, including: biological libraries; spatially addressable parallel solid phase or solution phase libraries; synthetic library methods requiring deconvolution; the 'one-bead one-compound' library method; and synthetic library methods using affinity chromatography selection. The biological library approach is limited to peptide libraries, while the other four approaches are applicable to peptide, non-peptide oligomer or small molecule libraries of compounds (Lam, K S. (1997) Anticancer Drug Des. 12:145).

Examples of methods for the synthesis of molecular libraries can be found in the art, for example in: DeWitt et al. (1993) Proc. Natl. Acad. Sci. USA 90:6909; Erb et al. (1994) Proc. Natl. Acad. Sci. USA 91:11422; Zuckermann et al. (1994) J. Med. Chem. 37:2678; Cho et al. (1993) Science 261:1303; Carrell et al. (1994) Angew. Chem. Int. Ed. Engl. 33:2059; Carell et al (1994) Angew. Chem. Int. Ed. Engl. 33:2061; and Gallop et al. (1994) J. Med. Chem. 37:1233.

Libraries of compounds may be presented in solution (e.g., Houghten (1992) Biotechniques 13:412-421), or on beads (Lam (1991) Nature 354:82-84), chips (Fodor (1993) Nature 364:555-556), bacteria (Ladner U.S. Pat. No. 5,223,409), spores (Ladner U.S. Pat. No. '409), plasmids (Cull et al. (1992) Proc. Natl. Acad. Sci. USA 89:1865-1869) or phage (Scott and Smith (1990) Science 249:386-390; Devlin (1990) Science 249:404-406; Cwirla et al. (1990) Proc. Natl. Acad. Sci. 87:6378-6382; Felici (1991) J. Mol. Biol. 222:301-310; Ladner supra.).

In one aspect, an assay is a cell-based assay in which a cell which expresses a GTRAP3-18 protein or biologically active portion thereof is contacted with a test compound, and the ability of the test compound to modulate GTRAP3-18 activity is determined. In a preferred embodiment, the biologically active portion of the GTRAP3-18 protein includes a domain or motif which can modulate glycosylation. Determining the ability of the test compound to modulate GTRAP3-18 activity can be accomplished by monitoring, for example, the glycosylation of one or more cellular proteins (e.g., EAAT proteins, GABA transporters, dopamine transporters, and/or amino acid transporters), or by measureing the activity of one or more proteins known to be regulated by glycosylation (e.g., EAAT proteins, GABA transporters, dopamine transporters, and/or amino acid transporters). The cell, for example, can be of mammalian origin, e.g., a neuronal cell.

The ability of the test compound to modulate GTRAP3-18 binding to a target molecule (e.g., a protein regulated by glycosylation, such as an EAAT protein, a GABA transporter, a dopamine transporters, and/or an amino acid transporter) can also be determined. Determining the ability of the test compound to modulate GTRAP3-18 binding to a target molecule can be accomplished, for example, by coupling the GTRAP3-18 target molecule with a radioisotope, fluorescent, or enzymatic label such that binding of the GTRAP3-18 target molecule to GTRAP3-18 can be determined by detecting the labeled GTRAP3-18 target molecule in a complex. Alternatively, GTRAP3-18 could be coupled with a radioisotope or enzymatic label to monitor the ability of a test compound to modulate GTRAP3-18 binding to a GTRAP3-18 target molecule in a complex. Determining the ability of the test compound to bind GTRAP3-18 can be accomplished, for example, by coupling the compound with a radioisotope or enzymatic label such that binding of the compound to GTRAP3-18 can be determined by detecting the labeled compound in a complex. For example, test compounds and/or GTRAP3-18 target molecules can be labeled with $^{125}I$ $^{35}S$, $^{14}C$, or $^{3}H$, either directly or indirectly, and the radioisotope detected by direct counting of radioemission or by scintillation counting. Alternatively, compounds can be enzymatically labeled with, for example, horseradish peroxidase, alkaline phosphatase, or luciferase, and the enzymatic label detected by determination of conversion of an appropriate substrate to product.

It is also within the scope of this invention to determine the ability of a compound to interact with GTRAP3-18 without the labeling of any of the interactants. For example, a microphysiometer can be used to detect the interaction of a compound with GTRAP3-18 and/or with a GTRAP-18 target molecule without the labeling of any of the interatants (McConnell, H. M. et al. (1992) Science 257:1906-1912). As used herein, a "microphysiometer" (e.g., Cytosensor) is an analytical instrument that measures the rate at which a cell acidifies its environment using a light-addressable potentiometric sensor (LAPS). Changes in this acidification rate can be used as an indicator of the interaction between a compound and GTRAP3-18.

Because GTRAP3-18 expression down-regulates glycosylation, compounds which modulate glycosylation can be identified by the ability to modulate GTRAP3-18 expression. To determine whether a test compound modulates GTRAP3-18 expression, a cell which expresses GTRAP3-18 (e.g., a neuronal cell) is contacted with a test compound, and the ability of the test compound to modulate GTRAP3-18 expression can be determined by measuring GTRAP3-18 mRNA by, e.g., Northern blotting, quantitative PCR (e.g., RT-PCR), or in vitro transcriptional assays. To perform an in vitro transcriptional assay, the full length promoter and enhancer of GTRAP3-18 can be linked to a reporter gene such as chloramphenicol acetyltransferase (CAT), luciferase, or a fluorescent protein (e.g., GFP and variants thereof) and introduced into host cells. The same host cells can then be transfected with or contacted with the test compound. The effect of the test compound can be measured by reporter gene activity and comparing it to reporter gene activity in cells which do not contain the test compound. An increase or decrease in reporter gene activity indicates a modulation of GTRAP3-18 expression and is, therefore, an indicator of the ability of the test compound to modulate glycosylation.

Assays that may be used to identify compounds that modulate GTRAP3-18 activity also include assays that test for the ability of a compound to modulate glycosylation of a GTRAP3-18 target molecule. The ability of a test compound to modulate glycosylation of a GTRAP3-18 target molecule can be measured, for example, using a "standard de-glycosylation assay". As used herein, a "standard de-glycosylation" assay comprises treating a protein (e.g., a GTRAP3-18 target molecule) with a deglycosylating enzyme such as PNGase F and/or Endo H. The treated protein is then compared with untreated control protein using an electrophoretic mobility shift assay. A difference in electrophoretic mobility (and thus in apparent molecular weight) between the treated and undtreated proteins reveals the degree to which the protein was originally glycosylated, prior to deglycosylation. That is, a protein that is not glycosylated will show no change in electrophoretic mobility after deglycosylase treatment, while a highly glycosylated protein will show a large change in electrophoretic mobility.

Further assays that may be used to identify compounds that modulate GTRAP3-18 activity include assays that test for the ability of a compound to modulate the activity of a GTRAP3-18 target molecule, for example, glutamate transporters, dopamine transporters, GABA transporters, and amino acid transporters.

Glutamate transporter activity can be measured using a standard glutamate transport assay. As used interchangeably herein the terms 'standard glutamate assay' or 'standard glutamate transport assay' (or like terms) are meant to include one or more of the following steps:
 a) introducing a recombinant expression vector comprising a glutamate transporter cDNA into suitable host cells such as COS-7 cells,
 b) adding detectably-labeled glutamate; and
 c) detecting glutamate transport in the cells.

Typically, the standard glutamate assay is a sodium-dependent glutamate transport assay. Introduction of the recombinant vectors in accord with the standard glutamate assay can be conducted by any acceptable means, e.g., retroviral transfer, viral or bacteriophage infection, calcium-, liposome-, DEAE or polybrene-mediated transfection, biolistic transfer, or other techniques known in the art. See Sambrook, et al. supra; Ausubel, et al. supra.

In one embodiment of the standard glutamate essay, the test and control cells are washed following introduction of the recombinant vector and then incubated with a suitable amount of detectably-labeled glutamate, e.g., 3H-labeled glutamate (DuPont-NEN) and non-labeled glutamate. Following a suitable incubation interval, test and control cells are washed several times in a suitable wash buffer such as ice-cold PBS, solublized in a solution comprising about 0.1% SDS and the amount of radioactivity associated with the cells determined using conventional scintillation counting methods.

An especially preferred glutamate transport assay has been disclosed by Rothstein et al. (1995) $Ann. Neurol.$ 38:78. See also Rothstein et al. (1992) $N. Engl. J. Med.$ 326: 1464. The disclosures of which are specifically incorporated by reference.

Exemplary methods for measuring GABA transport activity can be found in Karban, E. W. et al. (1991) Neuropharm. 30:1187-1192; and Falch, E. et al. (1986) J. Neuorchem. 47:898-903. Exemplary methods for measuring dopamine transport can be found in Janowski, A. et al. (1986) J. Neurochem. 46:1272-1276; and Brown, N. L. et al. (1986) Eur. J. Pharmacol. 123:161-165. Exemplary methods for measuring amino acid transport can be found in Zerangue, N. and Kavanaugh, M. P. (1996) J. Biol. Chem. 271:27991-27994. All of these references are incorporated herein by reference.

In yet another embodiment, an assay of the present invention is a cell-free assay in which a GTRAP3-18 protein or biologically active portion thereof is contacted with a test compound and the ability of the test compound to bind to or to modulate (e.g., stimulate or inhibit) the activity of the GTRAP3-18 protein or biologically active portion thereof is determined. Preferred biologically active portions of the GTRAP3-18 proteins to be used in assays of the present invention include fragments which participate in interactions with non-GTRAP3-18 molecules, e.g., EAAT proteins, GABA transporters, dopamine transporters, and amino acid transporters. Binding of the test compound to the GTRAP3-18 protein can be determined either directly or indirectly as described above. Determining the ability of the GTRAP3-18 protein to bind to a test compound can also be accomplished using a technology such as real-time Biomolecular Interaction Analysis (BIA) (Sjolander, S. and Urbaniczky, C. (1991) Anal Chem. 63:2338-2345; Szabo et al. (1995) Curr. Opin. Struct. Biol. 5:699-705). As used herein, "BIA" is a technology for studying biospecific interactions in real time, without labeling any of the interactants (e.g., BIAcore). Changes in the optical phenomenon of surface plasmon resonance (SPR) can be used as an indication of real-time reactions between biological molecules.

In yet another embodiment, the cell-free assay involves contacting a GTRAP3-18 protein or biologically active portion thereof with a known compound which binds the GTRAP3-18 protein (e.g., an EAAT protein, a GABA transporter, a dopamine transporter, or an amino acid transporter) to form an assay mixture, contacting the assay mixture with a test compound, and determining the ability of the test compound to interact with the GTRAP3-18 protein, wherein determining the ability of the test compound to interact with the GTRAP3-18 protein comprises determining the ability of the GTRAP3-18 protein to preferentially bind to or modulate the activity of a GTRAP3-18 target molecule.

The cell-free assays of the present invention are amenable to use of both soluble and/or membrane-bound forms of isolated proteins (e.g., EAAT proteins, GABA transporters, dopamine transporters, or amino acid transporters). In the case of cell-free assays in which a membrane-bound form of an isolated protein is used it may be desirable to utilize a solubilizing agent such that the membrane-bound form of the isolated protein is maintained in solution. Examples of such solubilizing agents include non-ionic detergents such as n-octylglucoside, n-dodecylglucoside, n-dodecylmaltoside, octanoyl-N-methylglucamide, decanoyl-N-methylglucamide, Triton® X-100, Triton® X-114, Thesit®, Isotridecypoly(ethylene glycol ether).sub.n, 3-[(3-cholamidopropyl)dimethylamminio]-1-propane sulfonate (CHAPS), 3-[(3-cholamidopropyl)dimethylamminio]-2-hydroxy-1-propane sulfonate (CHAPSO), or N-dodecyl=N,N-dimethyl-3-ammonio-1-propane sulfonate.

In more than one embodiment of the above assay methods of the present invention, it may be desirable to immobilize either GTRAP3-18 or a GTRAP3-18 target molecule to facilitate separation of complexed from uncomplexed forms of one or both of the proteins, as well as to accommodate automation of the assay. Binding of a test compound to a GTRAP3-18 protein, or interaction of a GTRAP3-18 protein with a GTRAP3-18 target molecule in the presence and absence of a test compound, can be accomplished in any vessel suitable for containing the reactants. Examples of such vessels include microtitre plates, test tubes, and micro-centrifuge tubes. In one embodiment, a fusion protein can be provided which adds a domain that allows one or both of the proteins to be bound to a matrix. For example, glutathione-S-transferase/GTRAP3-18 fusion proteins or glutathione-S-transferase/target fusion proteins can be adsorbed onto glutathione sepharose beads (Sigma Chemical, St. Louis, Mo.) or glutathione derivatized microtitre plates, which are then combined with the test compound or the test compound and either the non-adsorbed target protein or GTRAP3-18 protein, and the mixture incubated under conditions conducive to complex formation (e.g., at physiological conditions for salt and pH). Following incubation, the beads or microtitre plate wells are washed to remove any unbound components, the matrix is immobilized in the case of beads, and complex formation is determined either directly or indirectly, for example, as described above. Alternatively, the complexes can be dissociated from the matrix, and the level of GTRAP3-18 binding or activity determined using standard techniques.

Other techniques for immobilizing proteins or cell membrane preparations on matrices can also be used in the screening assays of the invention. For example, either a GTRAP3-18 protein or a GTRAP3-18 target molecule can be immobilized utilizing conjugation of biotin and streptavidin. Biotinylated GTRAP3-18 protein or target molecules can be prepared from biotin-NHS(N-hydroxy-succinimide) using techniques known in the art (e.g., biotinylation kit, Pierce Chemicals, Rockford, Ill.), and immobilized in the wells of streptavidin-coated 96 well plates (Pierce Chemical). Alternatively, antibodies which are reactive with GTRAP3-18 protein or target molecules but which do not interfere with binding of the GTRAP3-18 protein to its target molecule can be derivatized to the wells of the plate, and unbound target or GTRAP3-18 protein is trapped in the wells by antibody conjugation. Methods for detecting such complexes, in addition to those described above for the GST-immobilized complexes, include immunodetection of complexes using antibodies reactive with the GTRAP3-18 protein or target molecule, as well as enzyme-linked assays which rely on detecting an enzymatic activity associated with the GTRAP3-18 protein or target molecule.

In yet another aspect of the invention, the GTRAP3-18 protein or fragments thereof can be used as "bait proteins" in a two-hybrid assay or three-hybrid assay (see, e.g., U.S. Pat. No. 5,283,317; Zervos et al. (1993) Cell 72:223-232; Madura et al. (1993) J. Biol. Chem. 268:12046-12054; Bartel et al. (1993) Biotechniques 14:920-924; Iwabuchi et al. (1993) Oncogene 8:1693-1696; and Brent WO 94/10300) to identify other proteins which bind to or interact with GTRAP3-18 ("GTRAP3-18-binding proteins" or "GTRAP3-18-bp") and are involved in GTRAP3-18 activity. Such GTRAP3-18-binding proteins are likely to be glycosylated proteins, where the glycosylation is regulated by GTRAP-18. Alternatively, such GTRAP3-18-binding proteins may be GTRAP3-18 inhibitors.

The two-hybrid system is based on the modular nature of most transcription factors, which consist of separable DNA-binding and activation domains. Briefly, the assay utilizes two different DNA constructs. In one construct, the gene that codes for a GTRAP3-18 protein is fused to a gene encoding the DNA binding domain of a known transcription factor (e.g., GAL-4). In the other construct, a DNA sequence, from a library of DNA sequences, that encodes an unidentified protein ("prey" or "sample") is fused to a gene that codes for the activation domain of the known transcription factor. If the "bait" and the "prey" proteins are able to interact, in vivo, forming a GTRAP3-18-dependent complex, the DNA-binding and activation domains of the transcription factor are brought into close proximity. This proximity allows transcription of a reporter gene (e.g., LacZ) which is operably linked to a transcriptional regulatory site responsive to the transcription factor. Expression of the reporter gene can be detected and cell colonies containing the functional transcription factor can be isolated and used to obtain the cloned gene which encodes the protein which interacts with the GTRAP3-18 protein.

In another aspect, the invention pertains to a combination of two or more of the assays described herein. For example, a modulating agent can be identified using a cell-based or a cell-free assay, and the ability of the agent to modulate the activity of a GTRAP3-18 protein can be confirmed in vivo, e.g., in an animal such as an animal model for glycosylation associated disorder, e.g., a neurological disorder. Animals deficient in GTRAP3-18 (e.g., GTRAP3-18 knockout mice) may be deficient in the ability to regulate glycosylation and therefore may be useful in determining whether a test compound can regulate glycosylation by bypassing GTRAP3-18 and utilizing other pathways and/or regulators.

Moreover, a GTRAP3-18 modulator identified as described herein (e.g., an antisense GTRAP3-18 nucleic acid molecule, a GTRAP3-18-specific antibody, or a small molecule) can be used in an animal model to determine the efficacy, toxicity, or side effects of treatment with such a modulator. Alternatively, a GTRAP3-18 modulator identified as described herein can be used in an animal model to determine the mechanism of action of such a modulator.

II. Predictive Medicine:

The present invention also pertains to the field of predictive medicine in which diagnostic assays, prognostic assays, and monitoring clinical trials are used for prognostic (predictive) purposes to thereby treat an individual prophylactically. Accordingly, one aspect of the present invention relates to diagnostic assays for determining GTRAP3-18 protein and/or nucleic acid expression as well as GTRAP3-18 activity, in the context of a biological sample (e.g., blood, serum, cells, or tissue, e.g., muscle tissue) to thereby determine whether an individual is afflicted with a glycosylation associated disorder. The invention also provides for prognostic (or predictive) assays for determining whether an individual is at risk of developing a glycosylation associated disorder. For example, mutations in a GTRAP3-18 gene can be assayed for in a biological sample. Such assays can be used for prognostic or predictive purpose to thereby prophylactically treat an individual prior to the onset of a glycosylation associated disorder.

Another aspect of the invention pertains to monitoring the influence of GTRAP3-18 modulators (e.g., anti-GTRAP3-18 antibodies, ribozymes, or small molecules) on the expression or activity of GTRAP3-18 in clinical trials.

These and other agents are described in further detail in the following sections.

A. Diagnostic Assays for Glycosylation Associated Disorders

To determine whether a subject is afflicted with a glycosylation associated disorder, a biological sample may be obtained from a subject and the biological sample may be contacted with a compound or an agent capable of detecting a GTRAP3-18 protein or nucleic acid (e.g., mRNA or genomic DNA) that encodes a GTRAP3-18 protein, in the biological sample. A preferred agent for detecting GTRAP3-18 mRNA or genomic DNA is a labeled nucleic acid probe capable of hybridizing to GTRAP3-18 mRNA or genomic DNA. The nucleic acid probe can be, for example, the GTRAP3-18 nucleic acid set forth in SEQ ID NO:1, or a portion thereof, such as an oligonucleotide of at least 15, 20, 25, 30, 25, 40, 45, 50, 100, 250 or 500 nucleotides in length and sufficient to specifically hybridize under stringent conditions to GTRAP3-18 mRNA or genomic DNA. Other suitable probes for use in the diagnostic assays of the invention are described herein.

A preferred agent for detecting GTRAP3-18 protein in a sample is an antibody capable of binding to GTRAP3-18 protein, preferably an antibody with a detectable label. Antibodies can be polyclonal, or more preferably, monoclonal. An intact antibody, or a fragment thereof (e.g., Fab or F(ab')2) can be used. The term "labeled", with regard to the probe or antibody, is intended to encompass direct labeling of the probe or antibody by coupling (i.e., physically linking) a detectable substance to the probe or antibody, as well as indirect labeling of the probe or antibody by reactivity with another reagent that is directly labeled. Examples of direct substances that can be coupled to an antibody or a nucleic acid probe include various enzymes, prosthetic groups, fluorescent materials, luminescent materials, bioluminescent materials, and radioactive materials. Examples of indirect labeling include detection of a primary antibody using a fluorescently labeled secondary antibody and end-labeling of a DNA probe with biotin such that it can be detected with fluorescently labeled streptavidin.

The term "biological sample" is intended to include tissues, cells, and biological fluids isolated from a subject, as well as tissues, cells, and fluids present within a subject. That is, the detection method of the invention can be used to detect GTRAP3-18 mRNA, protein, or genomic DNA in a biological sample in vitro as well as in vivo. For example, in vitro techniques for detection of GTRAP3-18 mRNA include Northern hybridizations and in situ hybridizations. In vitro techniques for detection of GTRAP3-18 protein include enzyme linked immunosorbent assays (ELISAs), Western blots, immunoprecipitations and immunofluorescence. In vitro techniques for detection of GTRAP3-18 genomic DNA include Southern hybridizations. Furthermore, in vivo techniques for detection of GTRAP3-18 protein include introducing into a subject a labeled anti-GTRAP3-18 antibody. For example, the antibody can be labeled with a radioactive marker whose presence and location in a subject can be detected by standard imaging techniques.

In another embodiment, the methods further involve obtaining a control biological sample from a control subject, contacting the control sample with a compound or agent capable of detecting GTRAP3-18 protein, mRNA, or genomic DNA, such that the presence of GTRAP3-18 protein, mRNA or genomic DNA is detected in the biological sample, and comparing the presence of GTRAP3-18 protein, mRNA or genomic DNA in the control sample with the presence of GTRAP3-18 protein, mRNA or genomic DNA in the test sample.

B. Prognostic Assays for Glycosylation Associated Disorder

The present invention further pertains to methods for identifying subjects having or at risk of developing a glycosylation associated disorder with aberrant GTRAP3-18 expression or activity.

As used herein, the term "aberrant" includes a GTRAP3-18 expression or activity which deviates from the wild type GTRAP3-18 expression or activity. Aberrant expression or activity includes increased or decreased expression or activity, as well as expression or activity which does not follow the wild type developmental pattern of expression or the subcellular pattern of expression. For example, aberrant GTRAP3-18 expression or activity is intended to include the cases in which a mutation in the GTRAP3-18 gene causes the GTRAP3-18 gene to be under-expressed or over-expressed and situations in which such mutations result in a non-functional GTRAP3-18 protein or a protein which does not function in a wild-type fashion, e.g., a protein which does not interact with a GTRAP3-18 substrate, or one which interacts with a non-GTRAP3-18 substrate.

The assays described herein, such as the preceding diagnostic assays or the following assays, can be used to identify a subject having or at risk of developing a glycosylation associated disorder, e.g., a neurological disorder. A biological sample may be obtained from a subject and tested for the presence or absence of a genetic alteration. For example, such genetic alterations can be detected by ascertaining the existence of at least one of 1) a deletion of one or more nucleotides from a GTRAP3-18 gene, 2) an addition of one or more nucleotides to a GTRAP3-18 gene, 3) a substitution of one or more nucleotides of a GTRAP3-18 gene, 4) a chromosomal rearrangement of a GTRAP3-18 gene, 5) an alteration in the level of a messenger RNA transcript of a GTRAP3-18 gene, 6) aberrant modification of a GTRAP3-18 gene, such as of the methylation pattern of the genomic DNA, 7) the presence of a non-wild type splicing pattern of a messenger RNA transcript of a GTRAP3-18 gene, 8) a non-wild type level of a GTRAP3-18-protein, 9) allelic loss of a GTRAP3-18 gene, and 10) inappropriate post-translational modification of a GTRAP3-18-protein.

As described herein, there are a large number of assays known in the art which can be used for detecting genetic alterations in a GTRAP3-18 gene. For example, a genetic alteration in a GTRAP3-18 gene may be detected using a probe/primer in a polymerase chain reaction (PCR) (see, e.g., U.S. Pat. Nos. 4,683,195 and 4,683,202), such as anchor PCR or RACE PCR, or, alternatively, in a ligation chain reaction (LCR) (see, e.g., Landegran et al. (1988) Science 241:1077-1080; and Nakazawa et al. (1994) Proc. Natl. Acad. Sci. USA 91:360-364), the latter of which can be particularly useful for detecting point mutations in a GTRAP3-18 gene (see Abravaya et al. (1995) Nucleic Acids Res. 23:675-682). This method includes collecting a biological sample from a subject, isolating nucleic acid (e.g., genomic DNA, mRNA or both) from the sample, contacting the nucleic acid sample with one or more primers which specifically hybridize to a GTRAP3-18 gene under conditions such that hybridization and amplification of the GTRAP3-18 gene (if present) occurs, and detecting the presence or absence of an amplification product, or detecting the size of the amplification product and comparing the length to a control sample. It is anticipated that PCR and/or LCR may be desirable to use as a preliminary amplification step in conjunction with any of the techniques used for detecting mutations described herein.

Alternative amplification methods include: self sustained sequence replication (Guatelli, J. C. et al. (1990) Proc. Natl. Acad. Sci. USA 87:1874-1878), transcriptional amplification system (Kwoh, D. Y. et al (1989) Proc. Natl. Acad. Sci. USA 86:1173-1177), Q-Beta Replicase (Lizardi, P. M. et al. (1988) Bio-Technology 6:1197), or any other nucleic acid amplification method, followed by the detection of the amplified molecules using techniques well known to those of skill in the art. These detection schemes are especially useful for the detection of nucleic acid molecules if such molecules are present in very low numbers.

In an alternative embodiment, mutations in a GTRAP3-18 gene from a biological sample can be identified by alterations in restriction enzyme cleavage patterns. For example, sample and control DNA is isolated, amplified (optionally), digested with one or more restriction endonucleases, and fragment length sizes are determined by gel electrophoresis and compared. Differences in fragment length sizes between sample and control DNA indicates mutations in the sample DNA. Moreover, the use of sequence specific ribozymes (see, for example, U.S. Pat. No. 5,498,531) can be used to score for the presence of specific mutations by development or loss of a ribozyme cleavage site.

In other embodiments, genetic mutations in GTRAP3-18 can be identified by hybridizing biological sample derived and control nucleic acids, e.g., DNA or RNA, to high density arrays containing hundreds or thousands of oligonucleotide probes (Cronin, M. T. et al. (1996) Hum. Mutat. 7:244-255; Kozal, M. J. et al (1996) Nat. Med. 2:753-759). For example, genetic mutations in GTRAP3-18 can be identified in two dimensional arrays containing light-generated DNA probes as described in Cronin, M. T. et al. (1996) supra. Briefly, a first hybridization array of probes can be used to scan through long stretches of DNA in a sample and control to identify base changes between the sequences by making linear arrays of sequential, overlapping probes. This step allows for the identification of point mutations. This step is followed by a second hybridization array that allows for the characterization of specific mutations by using smaller, specialized probe arrays complementary to all variants or mutations detected. Each mutation array is composed of parallel probe sets, one complementary to the wild-type gene and the other complementary to the mutant gene.

In yet another embodiment, any of a variety of sequencing reactions known in the art can be used to directly sequence the GTRAP3-18 gene in a biological sample and detect mutations by comparing the sequence of the GTRAP3-18 in the biological sample with the corresponding wild-type (control) sequence. Examples of sequencing reactions include those based on techniques developed by Maxam and Gilbert (1977) Proc. Natl. Acad. Sci. USA 74:560) or Sanger (1977) Proc. Natl. Acad. Sci. USA 74:5463). It is also contemplated that any of a variety of automated sequencing procedures can be utilized when performing the diagnostic assays (Naeve, C. W. (1995) Biotechniques 19:448-53), including sequencing by mass spectrometry (see, e.g., PCT International Publication No. WO 94/16101; Cohen et al. (1996) Adv. Chromatogr. 36:127-162; and Griffin et al. (1993) Appl. Biochem. Biotechnol. 38:147-159).

Other methods for detecting mutations in the GTRAP3-18 gene include methods in which protection from cleavage agents is used to detect mismatched bases in RNA/RNA or RNA/DNA heteroduplexes (Myers et al. (1985) Science 230: 1242). In general, the art technique of "mismatch cleavage" starts by providing heteroduplexes formed by hybridizing (labeled) RNA or DNA containing the wild-type GTRAP3-18 sequence with potentially mutant RNA or DNA obtained from a tissue sample. The double-stranded duplexes are treated with an agent which cleaves single-stranded regions of the duplex such as which will exist due to basepair mismatches between the control and sample strands. For instance, RNA/DNA duplexes can be treated with RNase and DNA/DNA hybrids treated with S1 nuclease to enzymatically digest the mismatched regions. In other embodiments, either DNA/DNA or RNA/DNA duplexes can be treated with hydroxylamine or osmium tetroxide and with piperidine in order to digest mismatched regions. After digestion of the mismatched regions, the resulting material is then separated by size on denaturing polyacrylamide gels to determine the site of mutation. See, for example, Cotton et al. (1988) Proc. Natl. Acad. Sci. USA 85:4397 and Saleeba et al. (1992) Methods Enzymol. 217:286-295. In a preferred embodiment, the control DNA or RNA can be labeled for detection.

In still another embodiment, the mismatch cleavage reaction employs one or more proteins that recognize mismatched base pairs in double-stranded DNA (so called "DNA mismatch repair" enzymes) in defined systems for detecting and mapping point mutations in GTRAP3-18 cDNAs obtained from samples of cells. For example, the mutY enzyme of *E. coli* cleaves A at G/A mismatches and the thymidine DNA glycosylase from HeLa cells cleaves T at G/T mismatches (Hsu et al. (1994) Carcinogenesis 15:1657-1662). According to an exemplary embodiment, a probe based on a GTRAP3-18 sequence, e.g., a wild-type GTRAP3-18 sequence, is hybridized to a cDNA or other DNA product from a test cell(s). The duplex is treated with a DNA mismatch repair enzyme, and the cleavage products, if any, can be detected from electrophoresis protocols or the like. See, for example, U.S. Pat. No. 5,459,039.

In other embodiments, alterations in electrophoretic mobility will be used to identify mutations in GTRAP3-18 genes. For example, single strand conformation polymorphism (SSCP) may be used to detect differences in electrophoretic mobility between mutant and wild type nucleic acids (Orita et al. (1989) Proc Natl. Acad. Sci USA 86:2766; see also Cotton (1993) Mutat. Res. 285:125-144 and Hayashi (1992) Genet. Anal. Tech. Appl. 9:73-79). Single-stranded DNA fragments of sample and control GTRAP3-18 nucleic acids will be denatured and allowed to renature. The secondary structure of single-stranded nucleic acids varies according to sequence, the resulting alteration in electrophoretic mobility enables the detection of even a single base change. The DNA fragments may be labeled or detected with labeled probes. The sensitivity of the assay may be enhanced by using RNA (rather than DNA), in which the secondary structure is more sensitive to a change in sequence. In a preferred embodiment, the subject method utilizes heteroduplex analysis to separate double stranded heteroduplex molecules on the basis of changes in electrophoretic mobility (Keen et al. (1991) Trends Genet. 7:5).

In yet another embodiment the movement of mutant or wild-type fragments in polyacrylamide gels containing a gradient of denaturant is assayed using denaturing gradient gel electrophoresis (DGGE) ayers et al. (1985) Nature 313:495). When DGGE is used as the method of analysis, DNA will be modified to ensure that it does not completely denature, for example by adding a GC clamp of approximately 40 bp of high-melting GC-rich DNA by PCR. In a further embodiment, a temperature gradient is used in place of a denaturing gradient to identify differences in the mobility of control and sample DNA (Rosenbaum and Reissner (1987) Biophys. Chem. 265:12753).

Examples of other techniques for detecting point mutations include, but are not limited to, selective oligonucleotide hybridization, selective amplification, or selective primer extension. For example, oligonucleotide primers may be prepared in which the known mutation is placed centrally and then hybridized to target DNA under conditions which permit hybridization only if a perfect match is found (Saiki et al. (1986) Nature 324:163); Saiki et al. (1989) Proc. Natl. Acad. Sci. USA 86:6230). Such allele specific oligonucleotides are hybridized to PCR amplified target DNA or a number of different mutations when the oligonucleotides are attached to the hybridizing membrane and hybridized with labeled target DNA.

Alternatively, allele specific amplification technology which depends on selective PCR amplification may be used in conjunction with the instant invention. Oligonucleotides used as primers for specific amplification may carry the mutation of interest in the center of the molecule (so that amplification depends on differential hybridization) (Gibbs et al (1989) Nucleic Acids Res. 17:2437-2448) or at the extreme 3' end of one primer where, under appropriate conditions, mismatch can prevent, or reduce polymerase extension (Prossner (1993) Tibtech 11:238). In addition it may be desirable to introduce a novel restriction site in the region of the mutation to create cleavage-based detection (Gasparini et al. (1992) Mol. Cell Probes 6:1). It is anticipated that in certain embodiments amplification may also be performed using Taq ligase for amplification (Barany (1991) Proc. Natl. Acad. Sci USA 88:189). In such cases, ligation will occur only if there is a perfect match at the 3' end of the 5' sequence making it possible to detect the presence of a known mutation at a specific site by looking for the presence or absence of amplification.

Furthermore, the prognostic assays described herein can be used to determine whether a subject can be administered a GTRAP3-18 modulator (e.g., an agonist, antagonist, peptidomimetic, protein, peptide, nucleic acid, or small molecule) to effectively treat a glycosylation associated disorder.

C. Monitoring of Effects During Clinical Trials

The present invention further provides methods for determining the effectiveness of a GTRAP3-18 modulator (e.g., a GTRAP3-18 modulator identified herein) in treating a glycosylation associated disorder in a subject. For example, the effectiveness of a GTRAP3-18 modulator in increasing GTRAP3-18 gene expression, protein levels, or in upregulating GTRAP3-18 activity, can be monitored in clinical trials of subjects exhibiting decreased GTRAP3-18 gene expression, protein levels, or downregulated GTRAP3-18 activity. Alternatively, the effectiveness of a GTRAP3-18 modulator in decreasing GTRAP3-18 gene expression, protein levels, or in downregulating GTRAP3-18 activity, can be monitored in clinical trials of subjects exhibiting increased GTRAP3-18 gene expression, protein levels, or GTRAP3-18 activity. In such clinical trials, the expression or activity of a GTRAP3-18 gene, and preferably, other genes that have been implicated in, for example, a glycosylation associated disorder can be used as a "read out" or marker of the phenotype of a particular cell.

For example, and not by way of limitation, genes, including EAATs, GABA transporters, dopamine transporters, and/or amino acidtransportesr, that are modulated in cells by treatment with an agent which modulates GTRAP3-18 activity (e.g., identified in a screening assay as described herein) can be identified. Thus, to study the effect of agents which modulate GTRAP3-18 activity on subjects suffering from a glycosylation associated disorder in, for example, a clinical trial, cells can be isolated and RNA prepared and analyzed for the levels of expression of GTRAP3-18 and other genes implicated in the glycosylation associated disorder. The levels of gene expression (e.g., a gene expression pattern) can be quantified by Northern blot analysis or RT-PCR, as described herein, or alternatively by measuring the amount of protein produced, by one of the methods described herein, or by measuring the levels of activity of GTRAP3-18 or other genes (e.g., by measuring the level of glycosylation of cellular proteins such as EAATs, GABA transporters, dopamine transporters, and amino acid transporters). In this way, the gene expression pattern can serve as a marker, indicative of the physiological response of the cells to the agent which modulates GTRAP3-18 activity. This response state may be determined before, and at various points during treatment of the individual with the agent which modulates GTRAP3-18 activity.

In a preferred embodiment, the present invention provides a method for monitoring the effectiveness of treatment of a subject with an agent which modulates GTRAP3-18 activity (e.g., an agonist, antagonist, peptidomimetic, protein, peptide, nucleic acid, or small molecule identified by the screening assays described herein) including the steps of (i) obtaining a pre-administration sample from a subject prior to administration of the agent; (ii) detecting the level of expression of a GTRAP3-18 protein, mRNA, or genomic DNA in the pre-administration sample, or the level of glycosylation of a protein such as an EAAT in the pre-administration sample; (iii) obtaining one or more post-administration samples from the subject; (iv) detecting the level of expression or activity of the GTRAP3-18 protein, mRNA, or genomic DNA in the post-administration samples, or the level of glycosylation of a protein such as an EAAT in the post-administration sample; (v) comparing the level of expression or activity of the GTRAP3-18 protein, mRNA, or genomic DNA, or the level of glycosylation of a protein such as an EAAT in the pre-administration sample with the GTRAP3-18 protein, mRNA, or genomic DNA, or the level of glycosylation of a protein such as an EAAT in the post administration sample or samples; and (vi) altering the administration of the agent to the subject accordingly. For example, increased administration of the agent may be desirable to increase the expression or activity of GTRAP3-18 to higher levels than detected, i.e., to increase the effectiveness of the agent. Alternatively, decreased administration of the agent may be desirable to decrease expression or activity of GTRAP3-18 to lower levels than detected, i.e., to decrease the effectiveness of the agent. According to such an embodiment, GTRAP3-18 expression or activity may be used as an indicator of the effectiveness of an agent, even in the absence of an observable phenotypic response.

III. Methods of Treatment of Subjects Suffering from Glycosylation associated Disorders:

The present invention provides for both prophylactic and therapeutic methods of treating a subject, e.g., a human, at risk of (or susceptible to) a glycosylation associated disorder such as a neurological disorder. As used herein, "teatment" of a subject includes the application or administration of a therapeutic agent to a subject, or application or administration of a therapeutic agent to a cell or tissue from a subject, who has a diseases or disorders has a symptom of a disease or disorder, or is at risk of (or susceptible to) a disease or disorder, with the purpose to cure, heal, alleviate, relieve, alter, remedy, ameliorate, improve, or affect the disease or disorder, the symptom of the disease or disorder, or the risk of (or susceptibility to) the disease or disorder. As used herein, a "therapeutic agent" includes, but is not limited to, small molecules, peptides, polypeptides, antibodies, ribozymes, and antisense oligonucleotides.

A. Prophylactic Methods

In one aspect, the invention provides a method for preventing in a subject, a glycosylation associated disorder by administering to the subject an agent which modulates GTRAP3-18 expression or GTRAP3-18 activity, e.g., modulation of glycosylation in cells, e.g., neuronal cells. Subjects at risk for a glycosylation associated disorder can be identified by, for example, any or a combination of the diagnostic or prognostic assays described herein. Administration of a prophylactic agent can occur prior to the manifestation of symptoms characteristic of aberrant GTRAP3-18 expression or activity, such that a glycosylation associated disorder is prevented or, alternatively, delayed in its progression. Depending on the type of GTRAP3-18 aberrancy, for example, a GTRAP3-18 molecule, GTRAP3-18 agonist or GTRAP3-18 antagonist agent can be used for treating the subject. The appropriate agent can be determined based on screening assays described herein.

B. Therapeutic Methods

Another aspect of the invention pertains to methods for treating a subject suffering from a glycosylation associated disorder. These methods involve administering to a subject an agent which modulates GTRAP3-18 expression or activity (e.g., an agent identified by a screening assay described herein), or a combination of such agents. In another embodiment, the method involves administering to a subject a GTRAP3-18 protein or nucleic acid molecule as therapy to compensate for reduced, aberrant, or unwanted GTRAP3-18 expression or activity.

Stimulation of GTRAP3-18 activity is desirable in situations in which GTRAP3-18 is abnormally downregulated and/or in which increased GTRAP3-18 activity is likely to have a beneficial effect, i.e., a decrease in glycosylation, thereby ameliorating a glycosylation associated disorder associated with unwanted glycosylation. Likewise, inhibition of GTRAP3-18 activity is desirable in situations in which GTRAP3-18 is abnormally upregulated and/or in which decreased GTRAP3-18 activity is likely to have a beneficial effect, e.g., an increase in glycosylation, thereby ameliorating a glycosylation associated disorder associated with insufficient glycosylation.

The agents which modulate GTRAP3-18 activity can be administered to a subject using pharmaceutical compositions suitable for such administration. Such compositions typically comprise the agent (e.g., nucleic acid molecule, protein, or antibody) and a pharmaceutically acceptable carrier. As used herein the language "pharmaceutically acceptable carrier" is intended to include any and all solvents, dispersion media, coatings, antibacterial and antifungal agents, isotonic and absorption delaying agents, and the like, compatible with pharmaceutical administration. The use of such media and agents for pharmaceutically active substances is well known in the art. Except insofar as any conventional media or agent is incompatible with the active compound, use thereof in the compositions is contemplated. Supplementary active compounds can also be incorporated into the compositions.

A pharmaceutical composition used in the therapeutic methods of the invention is formulated to be compatible with its intended route of administration. Examples of routes of administration include parenteral, e.g., intravenous, intradermal, subcutaneous, oral (e.g., inhalation), transdermal (topical), transmucosal, and rectal administration. Solutions or suspensions used for parenteral, intradermal, or subcutaneous application can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. pH can be adjusted with acids or bases, such as hydrochloric acid or sodium hydroxide. The parenteral preparation can be enclosed in ampoules, disposable syringes or multiple dose vials made of glass or plastic.

Pharmaceutical compositions suitable for injectable use include sterile aqueous solutions (where water soluble) or dispersions and sterile powders for the extemporaneous preparation of sterile injectable solutions or dispersion. For intravenous administration, suitable carriers include physiological saline, bacteriostatic water, Cremophor EL™ (BASF, Parsippany, N.J.) or phosphate buffered saline (PBS). In all cases, the composition must be sterile and should be fluid to the extent that easy syringeability exists. It must be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, and liquid polyetheylene glycol, and the like), and suitable mixtures thereof. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. In many cases, it will be preferable to include isotonic agents, for example, sugars, polyalcohols such as manitol, sorbitol, and sodium chloride in the composition. Prolonged absorption of the injectable compositions can be brought about by including in the composition an agent which delays absorption, for example, aluminum monostearate and gelatin.

Sterile injectable solutions can be prepared by incorporating the agent that modulates GTRAP3-18 activity in the required amount in an appropriate solvent with one or a combination of ingredients enumerated above, as required, followed by filtered sterilization. Generally, dispersions are prepared by incorporating the active compound into a sterile vehicle which contains a basic dispersion medium and the required other ingredients from those enumerated above. In the case of sterile powders for the preparation of sterile injectable solutions, the preferred methods of preparation are vacuum drying and freeze-drying which yields a powder of the active ingredient plus any additional desired ingredient from a previously sterile-filtered solution thereof.

Oral compositions generally include an inert diluent or an edible carrier. They can be enclosed in gelatin capsules or compressed into tablets. For the purpose of oral therapeutic administration, the active compound can be incorporated with excipients and used in the form of tablets, troches, or capsules. Oral compositions can also be prepared using a fluid carrier for use as a mouthwash, wherein the compound in the fluid carrier is applied orally and swished and expectorated or swallowed. Pharmaceutically compatible binding agents, and/or adjuvant materials can be included as part of the composition. The tablets, pills, capsules, troches and the like can contain any of the following ingredients, or compounds of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate or Sterotes; a glidant such as colloidal silicon dioxide; a sweetening agent such as sucrose or saccharin; or a flavoring agent such as peppermint, methyl salicylate, or orange flavoring.

For administration by inhalation, the compounds are delivered in the form of an aerosol spray from pressured container or dispenser which contains a suitable propellant, e.g., a gas such as carbon dioxide, or a nebulizer.

Systemic administration can also be by transmucosal or transdermal means. For transmucosal or transdermal administration, penetrants appropriate to the barrier to be permeated are used in the formulation. Such penetrants are generally known in the art, and include, for example, for transmucosal administration, detergents, bile salts, and fusidic acid derivatives. Transmucosal administration can be accomplished through the use of nasal sprays or suppositories. For transdermal administration, the active compounds are formulated into ointments, salves, gels, or creams as generally known in the art.

The agents that modulate GTRAP3-18 activity can also be prepared in the form of suppositories (e.g., with conventional suppository bases such as cocoa butter and other glycerides) or retention enemas for rectal delivery.

In one embodiment, the agents that modulate GTRAP3-18 activity are prepared with carriers that will protect the compound against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art. The materials can also be obtained commercially from Alza Corporation and Nova Pharmaceuticals, Inc. Liposomal suspensions (including liposomes targeted to infected cells with monoclonal antibodies to viral antigens) can also be used as pharmaceutically acceptable carriers. These can be prepared according to methods known to those skilled in the art, for example, as described in U.S. Pat. No. 4,522,811.

It is especially advantageous to formulate oral or parenteral compositions in dosage unit form for ease of administration and uniformity of dosage. Dosage unit form as used herein refers to physically discrete units suited as unitary dosages for the subject to be treated; each unit containing a predetermined quantity of active compound calculated to produce the desired therapeutic effect in association with the required pharmaceutical carrier. The specification for the dosage unit forms of the invention are dictated by and directly dependent on the unique characteristics of the agent that modulates GTRAP3-18 activity and the particular therapeutic effect to be achieved, and the limitations inherent in the art of compounding such an agent for the treatment of subjects.

Toxicity and therapeutic efficacy of such agents can be determined by standard pharmaceutical procedures in cell cultures or experimental animals, e.g., for determining the LD50 (the dose lethal to 50% of the population) and the ED50 (the dose therapeutically effective in 50% of the population). The dose ratio between toxic and therapeutic effects is the therapeutic index and can be expressed as the ratio LD50/ED50. Agents which exhibit large therapeutic indices are preferred. While agents that exhibit toxic side effects may be used, care should be taken to design a delivery system that targets such agents to the site of affected tissue in order to minimize potential damage to uninfected cells and, thereby, reduce side effects.

The data obtained from the cell culture assays and animal studies can be used in formulating a range of dosage for use in humans. The dosage of such GTRAP3-18 modulating agents lies preferably within a range of circulating concentrations that include the ED50 with little or no toxicity. The dosage may vary within this range depending upon the dosage form employed and the route of administration utilized. For any agent used in the therapeutic methods of the invention, the therapeutically effective dose can be estimated initially from cell culture assays. A dose may be formulated in animal models to achieve a circulating plasma concentration range that includes the IC50 (i.e., the concentration of the test compound which achieves a half-maximal inhibition of symptoms) as determined in cell culture. Such information can be used to more accurately determine useful doses in humans. Levels in plasma may be measured, for example, by high performance liquid chromatography.

As defined herein, a therapeutically effective amount of protein or polypeptide (i.e., an effective dosage) ranges from about 0.001 to 30 mg/kg body weight, preferably about 0.01 to 25 mg/kg body weight, more preferably about 0.1 to 20 mg/kg body weight, and even more preferably about 1 to 10 mg/kg, 2 to 9 mg/kg, 3 to 8 mg/kg, 4 to 7 mg/kg, or 5 to 6 mg/kg body weight. The skilled artisan will appreciate that certain factors may influence the dosage required to effectively treat a subject, including but not limited to the severity of the disease or disorder, previous treatments, the general health and/or age of the subject, and other diseases present. Moreover, treatment of a subject with a therapeutically effective amount of a protein, polypeptide, or antibody can include a single treatment or, preferably, can include a series of treatments.

In a preferred example, a subject is treated with antibody, protein, or polypeptide in the range of between about 0.1 to 20 mg/kg body weight, one time per week for between about 1 to 10 weeks, preferably between 2 to 8 weeks, more preferably between about 3 to 7 weeks, and even more preferably for about 4, 5, or 6 weeks. It will also be appreciated that the effective dosage of antibody, protein, or polypeptide used for treatment may increase or decrease over the course of a particular treatment. Changes in dosage may result and become apparent from the results of diagnostic assays as described herein.

The present invention encompasses agents which modulate expression or activity. An agent may, for example, be a small molecule. For example, such small molecules include, but are not limited to, peptides, peptidomimetics, amino acids, amino acid analogs, polynucleotides, polynucleotide analogs, nucleotides, nucleotide analogs, organic or inorganic compounds (i.e., including heteroorganic and organometallic compounds) having a molecular weight less than about 10,000 grams per mole, organic or inorganic compounds having a molecular weight less than about 5,000 grams per mole, organic or inorganic compounds having a molecular weight less than about 1,000 grams per mole, organic or inorganic compounds having a molecular weight less than about 500 grams per mole, and salts, esters, and other pharmaceutically acceptable forms of such compounds. It is understood that appropriate doses of small molecule agents depends upon a number of factors within the ken of the ordinarily skilled physician, veterinarian, or researcher. The dose(s) of the small molecule will vary, for example, depending upon the identity, size, and condition of the subject or sample being treated, further depending upon the route by which the composition is to be administered, if applicable, and the effect which the practitioner desires the small molecule to have upon the nucleic acid or polypeptide of the invention. Exemplary doses include milligram or microgram amounts of the small molecule per kilogram of subject or sample weight (e.g., about 1 microgram per kilogram to about 500 milligrams per kilogram, about 100 micrograms per kilogram to about 5 milligrams per kilogram, or about 1 microgram per kilogram to about 50 micrograms per kilogram). It is furthermore understood that appropriate doses of a small molecule depend upon the potency of the small molecule with respect to the expression or activity to be modulated. Such appropriate doses may be determined using the assays described herein. When one or more of these small molecules is to be administered to an animal (e.g., a human) in order to modulate expression or activity of a polypeptide or nucleic acid of the invention, a physician, veterinarian, or researcher may, for example, prescribe a relatively low dose at first, subsequently increasing the dose until an appropriate response is obtained. In addition, it is understood that the specific dose level for any particular animal subject will depend upon a variety of factors including the activity of the specific compound employed, the age, body weight, general health, gender, and diet of the subject, the time of administration, the route of administration, the rate of excretion, any drug combination, and the degree of expression or activity to be modulated.

Further, an antibody (or fragment thereof) may be conjugated to a therapeutic moiety such as a cytotoxin, a therapeutic agent or a radioactive metal ion. A cytotoxin or cytotoxic agent includes any agent that is detrimental to cells. Examples include taxol, cytochalasin B, gramicidin D, ethidium bromide, emetine, mitomycin, etoposide, tenoposide, vincristine, vinblastine, colchicin, doxorubicin, daunorubicin, dihydroxy anthracin dione, mitoxantrone, mithramycin, actinomycin D, 1-dehydrotestosterone, glucocorticoids, procaine, tetracaine, lidocaine, propranolol, and puromycin and analogs or homologs thereof. Therapeutic agents include, but are not limited to, antimetabolites (e.g., methotrexate, 6-mercaptopurine, 6-thioguanine, cytarabine, 5-fluorouracil decarbazine), alkylating agents (e.g., mechlorethamine, thioepa chlorambucil, melphalan, carmustine (BSNU) and lomustine (CCNU), cyclothosphamide, busulfan, dibromomannitol, streptozotocin, mitomycin C, and cis-dichlorodiamine platinum (II) (DDP) cisplatin), anthracyclines (e.g., daunorubicin (formerly daunomycin) and doxorubicin), antibiotics (e.g., dactinomycin (formerly actinomycin), bleomycin, mithramycin, and anthramycin (AMC)), and anti-mitotic agents (e.g., vincristine and vinblastine).

The conjugates of the invention can be used for modifying a given biological response, the drug moiety is not to be construed as limited to classical chemical therapeutic agents. For example, the drug moiety may be a protein or polypeptide possessing a desired biological activity. Such proteins may include, for example, a toxin such as abrin, ricin A, pseudomonas exotoxin, or diphtheria toxin; a protein such as tumor necrosis factor, alpha-interferon, beta-interferon, nerve growth factor, platelet derived growth factor, tissue plasminogen activator; or biological response modifiers such as, for example, lymphokines, interleukin-1 ("IL-1"), interleukin-2 ("IL-2"), interleukin-6 ("IL-6"), granulocyte macrophage colony stimulating factor ("GM-CSF"), granulocyte colony stimulating factor ("G-CSF"), or other growth factors.

Techniques for conjugating such therapeutic moiety to antibodies are well known, see, e.g., Amon et al., "Monoclonal Antibodies for Immunotargeting of Drugs in Cancer Therapy", in Monoclonal Antibodies and Cancer Therapy, Reisfeld et al. (eds.), pp. 243-56 (Alan R. Liss, Inc. 1985); Hellstrom et al., "Antibodies for Drug Delivery", in Controlled Drug Delivery (2nd Ed.), Robinson et al. (eds.), pp. 623-53 (Marcel Dekker, Inc. 1987); Thorpe, "Antibody Carriers of Cytotoxic Agents in Cancer Therapy: A Review", in Monoclonal Antibodies '84: Biological and Clinical Applications, Pinchera et al. (eds.), pp. 475-506 (1985); "Analysis, Results, and Future Prospective of the Therapeutic Use of Radiolabeled Antibody in Cancer Therapy", in Monoclonal Antibodies for Cancer Detection and Therapy, Baldwin et al. (eds.), pp. 303-16 (Academic Press 1985), and Thorpe et al. (1982) "The Preparation and Cytotoxic Properties of Antibody-Toxin Conjugates", Immunol. Rev. 62:119-58. Alternatively, an antibody can be conjugated to a second antibody to form an antibody heteroconjugate as described by Segal in U.S. Pat. No. 4,676,980.

The nucleic acid molecules used in the methods of the invention can be inserted into vectors and used as gene therapy vectors. Gene therapy vectors can be delivered to a subject by, for example, intravenous injection, local administration (see U.S. Pat. No. 5,328,470) or by stereotactic injection (see, e.g., Chen et al. (1994) Proc. Natl. Acad. Sci. USA 91:3054-3057). The pharmaceutical preparation of the gene therapy vector can include the gene therapy vector in an acceptable diluent, or can comprise a slow release matrix in which the gene delivery vehicle is imbedded. Alternatively, where the complete gene delivery vector can be produced intact from recombinant cells, e.g., retroviral vectors, the pharmaceutical preparation can include one or more cells which produce the gene delivery system.

IV. Recombinant Expression Vectors and Host Cells Used in the Methods of the Invention The methods of the invention (e.g., the screening assays described herein) include the use of vectors, preferably expression vectors, containing nucleic acid molecules encoding a GTRAP3-18 protein (or a portion thereof), as well as GTRAP3-18 target molecules (e.g., EAATs, GABA transporters, dopamine transporters, or amino acid transporters), or portions thereof. As used herein, the term "vector" refers to a nucleic acid molecule capable of transporting another nucleic acid to which it has been linked. One type of vector is a "plasmid", which refers to a circular double stranded DNA loop into which additional DNA segments can be ligated. Another type of vector is a viral vector, wherein additional DNA segments can be ligated into the viral genome. Certain vectors are capable of autonomous replication in a host cell into which they are introduced (e.g., bacterial vectors having a bacterial origin of replication and episomal mammalian vectors). Other vectors (e.g., non-episomal mammalian vectors) are integrated into the genome of a host cell upon introduction into the host cell, and thereby are replicated along with the host genome. Moreover, certain vectors are capable of directing the expression of genes to which they are operatively linked. Such vectors are referred to herein as "expression vectors". In general, expression vectors of utility in recombinant DNA techniques are often in the form of plasmids. In the present specification, "plasmid" and "vector" can be used interchangeably as the plasmid is the most commonly used form of vector. However, the invention is intended to include such other forms of expression vectors, such as viral vectors (e.g., replication defective retroviruses, adenoviruses and adeno-associated viruses), which serve equivalent functions.

The recombinant expression vectors to be used in the methods of the invention comprise a nucleic acid of the invention in a form suitable for expression of the nucleic acid in a host cell, which means that the recombinant expression vectors include one or more regulatory sequences, selected on the basis of the host cells to be used for expression, which is operatively linked to the nucleic acid sequence to be expressed. Within a recombinant expression vector, "operably linked" is intended to mean that the nucleotide sequence of interest is linked to the regulatory sequence(s) in a manner which allows for expression of the nucleotide sequence (e.g., in an in vitro transcription/translation system or in a host cell when the vector is introduced into the host cell). The term "regulatory sequence" is intended to include promoters, enhancers and other expression control elements (e.g., polyadenylation signals). Such regulatory sequences are described, for example, in Goeddel (1990) Methods Enzymol. 185:3-7. Regulatory sequences include those which direct constitutive expression of a nucleotide sequence in many types of host cells and those which direct expression of the nucleotide sequence only in certain host cells (e.g., tissue-specific regulatory sequences). It will be appreciated by those skilled in the art that the design of the expression vector can depend on such factors as the choice of the host cell to be transformed, the level of expression of protein desired, and the like. The expression vectors of the invention can be introduced into host cells to thereby produce proteins or peptides, including fusion proteins or peptides, encoded by nucleic acids as described herein (e.g., GTRAP3-18 proteins, GTRAP3-18 target molecules, mutant forms of GTRAP3-18 proteins and/or GTRAP3-18 target molecules, fusion proteins, and the like).

The recombinant expression vectors to be used in the methods of the invention can be designed for expression of GTRAP3-18 proteins in prokaryotic or eukaryotic cells. For example, GTRAP3-18 proteins can be expressed in bacterial cells such as *E. coli*, insect cells (using baculovirus expression vectors), yeast cells, or mammalian cells. Suitable host cells are discussed further in Goeddel (1990) supra. Alternatively, the recombinant expression vector can be transcribed and translated in vitro, for example using 17 promoter regulatory sequences and T7 polymerase.

Expression of proteins in prokaryotes is most often carried out in *E. coli* with vectors containing constitutive or inducible promoters directing the expression of either fusion or non-fusion proteins. Fusion vectors add a number of amino acids to a protein encoded therein, usually to the amino terminus of the recombinant protein. Such fusion vectors typically serve three purposes: 1) to increase expression of recombinant protein; 2) to increase the solubility of the recombinant protein;

and 3) to aid in the purification of the recombinant protein by acting as a ligand in affinity purification. Often, in fusion expression vectors, a proteolytic cleavage site is introduced at the junction of the fusion moiety and the recombinant protein to enable separation of the recombinant protein from the fusion moiety subsequent to purification of the fusion protein. Such enzymes, and their cognate recognition sequences, include Factor Xa, thrombin and enterokinase. Typical fusion expression vectors include pGEX (Pharmacia Biotech Inc; Smith, D. B. and Johnson, K. S. (1988) Gene 67:31-40), pMAL (New England Biolabs, Beverly, Mass.) and pRIT5 (Pharmacia, Piscataway, N.J.) which fuse glutathione S-transferase (GST), maltose E binding protein, or protein A, respectively, to the target recombinant protein.

Purified fusion proteins can be utilized in GTRAP3-18 activity assays (e.g., direct assays or competitive assays described in detail below), or to generate antibodies specific for GTRAP3-18 proteins. In a preferred embodiment, a GTRAP3-18 fusion protein expressed in a retroviral expression vector of the present invention can be utilized to infect bone marrow cells which are subsequently transplanted into irradiated recipients. The pathology of the subject recipient is then examined after sufficient time has passed (e.g., six weeks).

In another embodiment, a nucleic acid of the invention is expressed in mammalian cells using a mammalian expression vector. Examples of mammalian expression vectors include pCDM8 (Seed, B. (1987) Nature 329:840) and pMT2PC (Kaufman et al. (1987) EMBO J. 6:187-195). When used in mammalian cells, the expression vector's control functions are often provided by viral regulatory elements. For example, commonly used promoters are derived from polyoma, Adenovirus 2, cytomegalovirus and Simian Virus 40. For other suitable expression systems for both prokaryotic and eukaryotic cells see chapters 16 and 17 of Sambrook, J. et al., Molecular Cloning: A Laboratory Manual. 2nd ed., Cold Spring Harbor Laboratory, Cold Spring Harbor Laboratory Press, Cold Spring Harbor, N.Y., 1989.

In another embodiment, the recombinant mammalian expression vector is capable of directing expression of the nucleic acid preferentially in a particular cell type (e.g., tissue-specific regulatory elements are used to express the nucleic acid).

The methods of the invention may further use a recombinant expression vector comprising a DNA molecule of the invention cloned into the expression vector in an antisense orientation. That is, the DNA molecule is operatively linked to a regulatory sequence in a manner which allows for expression (by transcription of the DNA molecule) of an RNA molecule which is antisense to GTRAP3-18 mRNA. Regulatory sequences operatively linked to a nucleic acid cloned in the antisense orientation can be chosen which direct the continuous expression of the antisense RNA molecule in a variety of cell types, for instance viral promoters and/or enhancers, or regulatory sequences can be chosen which direct constitutive, tissue specific, or cell type specific expression of antisense RNA. The antisense expression vector can be in the form of a recombinant plasmid, phagemid, or attenuated virus in which antisense nucleic acids are produced under the control of a high efficiency regulatory region, the activity of which can be determined by the cell type into which the vector is introduced. For a discussion of the regulation of gene expression using antisense genes, see Weintraub, H. et al., Antisense RNA as a molecular tool for genetic analysis, Reviews—Trends in Genetics, Vol. 1(1) 1986.

Another aspect of the invention pertains to the use of host cells into which a GTRAP3-18 or GTRAP3-18 target molecule (such as an EAAT, a GABA transporter, a dopamine transporter, or an amino acid transporter) nucleic acid molecule of the invention is introduced, e.g., a GTRAP3-18 or GTRAP3-18 target molecule nucleic acid molecule within a recombinant expression vector or a GTRAP3-18 or GTRAP3-18 target molecule nucleic acid molecule containing sequences which allow it to homologously recombine into a specific site of the host cell's genome. The terms "host cell" and "recombinant host cell" are used interchangeably herein. It is understood that such terms refer not only to the particular subject cell but to the progeny or potential progeny of such a cell. Because certain modifications may occur in succeeding generations due to either mutation or environmental influences, such progeny may not, in fact, be identical to the parent cell, but are still included within the scope of the term as used herein.

A host cell can be any prokaryotic or eukaryotic cell. For example, a GTRAP3-18 protein or GTRAP3-18 target molecule can be expressed in bacterial cells such as *E. coli*, insect cells, yeast or mammalian cells (such as Chinese hamster ovary cells (CHO) or COS cells). Other suitable host cells are known to those skilled in the art.

Vector DNA can be introduced into prokaryotic or eukaryotic cells via conventional transformation or transfection techniques. As used herein, the terms "transformation" and "transfection" are intended to refer to a variety of art-recognized techniques for introducing foreign nucleic acid (e.g., DNA) into a host cell, including calcium phosphate or calcium chloride co-precipitation, DEAE-dextran-mediated transfection, lipofection, or electroporation. Suitable methods for transforming or transfecting host cells can be found in Sambrook et al. (Molecular Cloning: A Laboratory Manual. 2.sup.nd. ed., Cold Spring Harbor Laboratory, Cold Spring Harbor Laboratory Press, Cold Spring Harbor, N.Y., 1989), and other laboratory manuals.

A host cell used in the methods of the invention, such as a prokaryotic or eukaryotic host cell in culture, can be used to produce (i.e., express) a GTRAP3-18 protein or GTRAP3-18 target molecule. Accordingly, the invention further provides methods for producing a GTRAP3-18 protein or GTRAP3-18 target molecule using the host cells of the invention. In one embodiment, the method comprises culturing the host cell of the invention (into which a recombinant expression vector encoding a GTRAP3-18 protein or GTRAP3-18 target molecule has been introduced) in a suitable medium such that a GTRAP3-18 protein or GTRAP3-18 target molecule is produced. In another embodiment, the method further comprises isolating a GTRAP3-18 protein or GTRAP3-18 target molecule from the medium or the host cell.

V. Isolated Nucleic Acid Molecules Used in the Methods of the Invention

The cDNA sequence of the isolated rat GTRAP3-18 gene and the predicted amino acid sequence of the rat GTRAP3-18 polypeptide are shown in SEQ ID NOs:1 and 2, respectively, and in FIG. 1 (coding sequence and polypeptide only), and are described in Lin, C.-I. Et al. (2001) Nature 410:84-88; GenBank Accession No. NM_023972; PCT International Publication No. WO 01/30968; as well as in U.S. patent application Ser. No. 09/695,795. The cDNA sequence of the isolated mouse GTRAP3-18 is described in Butchbach, M. E. et al. (2002) Gene 292(1-2):81-90 and in Gene GenBank Accession No. NM_022992. The cDNA sequence of the isolated human GTRAP3-18 is described in Butchbach, M. E. et al. (2002) Gene 292(1-2):81-90. The contents of all of the above-referenced publications are herein incorporated by reference.

The methods of the invention also use isolated nucleic acid molecules that encode GTRAP3-18 target molecules, i.e., proteins which GTRAP3-18 interacts with and/or modulates the glycosylation of GTRAP3-18 target molecules may be any protein that is or can be glycosylated. In a preferred embodiment, a GTRAP3-18 target molecule is a glutamate transporter such as GLAST/EAAT1, GLT-1/EAAT2, EAAC1/EAAT3, EAAT4, or EAAT5. In another embodiment, a GTRAP3-18 target molecule is a GABA transporter (e.g., GAT), a dopamine transporter (e.g., DAT), or an amino acid transporter (e.g., ASCT). Nucleic acid and polypeptide sequences for any of these types of transporters are well-known in the art.

The methods of the invention include the use of isolated nucleic acid molecules that encode GTRAP3-18 proteins and GTRAP3-18 target molecules or biologically active portions thereof, as well as nucleic acid fragments sufficient for use as hybridization probes to identify GTRAP3-18-encoding and GTRAP3-18 target molecule-encoding nucleic acid molecules (e.g., GTRAP3-18 and GTRAP3-18 target molecule mRNA) and fragments for use as PCR primers for the amplification or mutation of GTRAP3-18 and GTRAP3-18 target molecule nucleic acid molecules. As used herein, the term "nucleic acid molecule" is intended to include DNA molecules (e.g., cDNA or genomic DNA) and RNA molecules (e.g., mRNA) and analogs of the DNA or RNA generated using nucleotide analogs. The nucleic acid molecule can be single-stranded or double-stranded, but preferably is double-stranded DNA.

A nucleic acid molecule used in the methods of the present invention, e.g., a GTRAP3-18 or GTRAP3-18 target molecule nucleic acid molecule, or a portion thereof, can be isolated using standard molecular biology techniques and the sequence information provided herein. Using all or portion of the nucleic acid sequence of a GTRAP3-18 or GTRAP3-18 target molecule nucleic acid molecule as a hybridization probe, a GTRAP3-18 or GTRAP3-18 target molecule nucleic acid molecule can be isolated using standard hybridization and cloning techniques (e.g., as described in Sambrook, J. et al., Molecular Cloning: A Laboratory Manual. 2nd. ed., Cold Spring Harbor Laboratory, Cold Spring Harbor Laboratory Press, Cold Spring Harbor, N.Y., 1989).

Moreover, a nucleic acid molecule encompassing all or a portion of a GTRAP3-18 or GTRAP3-18 target molecule nucleic acid molecule can be isolated by the polymerase chain reaction (PCR) using synthetic oligonucleotide primers designed based upon the sequence of a GTRAP3-18 or GTRAP3-18 target molecule nucleic acid molecule (e.g., the nucleic acid sequence of SEQ ID NO:1).

A nucleic acid used in the methods of the invention can be amplified using DNA, mRNA or, alternatively, genomic DNA as a template and appropriate oligonucleotide primers according to standard PCR amplification techniques. Furthermore, oligonucleotides corresponding to GTRAP3-18 or GTRAP3-18 target molecule nucleotide sequences can be prepared by standard synthetic techniques, e.g., using an automated DNA synthesizer.

In a preferred embodiment, the isolated nucleic acid molecules used in the methods of the invention comprise the nucleotide sequence shown in SEQ ID NO:1, a complement of the nucleotide sequence shown in SEQ ID NO:1, or a portion of any of these nucleotide sequences. A nucleic acid molecule which is complementary to the nucleotide sequence shown in SEQ ID NO:1, is one which is sufficiently complementary to the nucleotide sequence shown in SEQ ID NO:1 such that it can hybridize to the nucleotide sequence shown in SEQ ID NO:1, thereby forming a stable duplex.

In still another preferred embodiment, an isolated nucleic acid molecule used in the methods of the present invention comprises a nucleotide sequence which is at least about 55%, 60%, 65%, 70%, 75%, 80%, 85%, 90%, 95%, 96%, 97%, 98%, 99%, 99.1%, 99.2%, 99.3%, 99.4%, 99.5%, 99.6%, 99.7%, 99.8%, 99.9% or more identical to the entire length of the nucleotide sequence shown in SEQ ID NO:1, or a portion of any of this nucleotide sequence.

Moreover, the nucleic acid molecules used in the methods of the invention can comprise only a portion of the nucleic acid sequence of a GTRAP3-18 or GTRAP3-18 target molecule nucleic acid molecule, for example, a fragment which can be used as a probe or primer or a fragment encoding a portion of a a GTRAP3-18 protein or GTRAP3-18 target molecule, e.g., a biologically active portion of a GTRAP3-18 protein or GTRAP3-18 target molecule. The probe/primer typically comprises substantially purified oligonucleotide. The oligonucleotide typically comprises a region of nucleotide sequence that hybridizes under stringent conditions to at least about 12 or 15, preferably about 20 or 25, more preferably about 30, 35, 40, 45, 50, 55, 60, 65, or 75 consecutive nucleotides of a sense sequence of SEQ ID NO:1 or an antisense sequence of SEQ ID NO:1, or of a naturally occurring allelic variant or mutant of SEQ ID NO:1. In one embodiment, a nucleic acid molecule used in the methods of the present invention comprises a nucleotide sequence which is greater than 50, 50-100, 100-200, 200-300, 300-400, 400-500, 500-600, 600-700, 700-800, 800-900, 900-1000, 1000-1100 or more nucleotides in length and hybridizes under stringent hybridization conditions to a nucleic acid molecule of SEQ ID NO:1.

As used herein, the term "hybridizes under stringent conditions" is intended to describe conditions for hybridization and washing under which nucleotide sequences that are significantly identical or homologous to each other remain hybridized to each other. Preferably, the conditions are such that sequences at least about 70%, more preferably at least about 80%, even more preferably at least about 85% or 90% identical to each other remain hybridized to each other. Such stringent conditions are known to those skilled in the art and can be found in Current Protocols in Molecular Biology, Ausubel et al., eds., John Wiley & Sons, Inc. (1995), sections 2, 4 and 6. Additional stringent conditions can be found in Molecular Cloning: A Laboratory Manual, Sambrook et al., Cold Spring Harbor Press, Cold Spring Harbor, N.Y. (1989), chapters 7, 9 and 11. A preferred, non-limiting example of stringent hybridization conditions includes hybridization in 4× or 6× sodium chloride/sodium citrate (SSC), at about 65-70° C. (or hybridization in 4×SSC plus 50% formamide at about 42-50° C.) followed by one or more washes in 1×SSC, at about 65-70° C. A further preferred, non-limiting example of stringent hybridization conditions includes hybridization at 6×SSC at 45° C., followed by one or more washes in 0.2×SSC, 0.1% SDS at 65° C. A preferred, non-limiting example of highly stringent hybridization conditions includes hybridization in 1×SSC, at about 65-70° C. (or hybridization in 1×SSC plus 50% formamide at about 42-50° C.) followed by one or more washes in 0.3×SSC, at about 65-70° C. A preferred, non-limiting example of reduced stringency hybridization conditions includes hybridization in 4× or 6×SSC, at about 50-60° C. (or alternatively hybridization in 6×SSC plus 50% formamide at about 4045° C.) followed by one or more washes in 2×SSC, at about 50-60° C. Ranges intermediate to the above-recited values, e.g., at 65-70° C. or at 42-50° C. are also intended to be encompassed by the present invention. SSPE (1×SSPE is 0.15M NaCl, 10 mM NaH$_2$PO$_4$, and 1.25 MM EDTA, pH 7.4) can be substituted for SSC (1×SSC is 0.15M NaCl and 15 mM sodium citrate) in the hybridization and wash buffers; washes are performed for 15 minutes each after hybridization is complete. The hybridization temperature for hybrids anticipated to be less than 50 base pairs in length should be 5-10° C. less than the melting temperature ($T_m$) of the hybrid, where $T_m$ is determined according to the following equations. For hybrids less than 18 base pairs in length, $T_m(° C.)=2(\# \text{ of A+T bases})+4(\# \text{ of G+C bases})$. For hybrids between 18 and 49 base pairs in length, $T_m(° C.)=81.5+16.6(\log 10[Na+])+0.41(\% \text{ G+C})-(600/N)$, where N is the number of bases in the hybrid, and [Na+] is the concentration of sodium ions in the hybridization buffer ([Na+] for 1×SSC=0.165 M). It will also be recognized by the skilled practitioner that additional reagents may be added to hybridization and/or wash buffers to decrease non-specific hybridization of nucleic acid molecules to membranes, for example, nitrocellulose or nylon membranes, including but not limited to blocking agents (e.g., BSA or salmon or herring sperm carrier DNA), detergents (e.g., SDS), chelating agents (e.g., EDTA), Ficoll, PVP and the like. When using nylon membranes, in particular, an additional preferred, non-limiting example of stringent hybridization conditions is hybridization in 0.25-0.5M NaH2PO4, 7% SDS at about 65° C., followed by one or more washes at 0.02M NaH2PO4, 1% SDS at 65° C., see e.g., Church and Gilbert (1984) Proc. Natl. Acad. Sci. USA 81:1991-1995 (or alternatively 0.2×SSC, 1% SDS).

In preferred embodiments, the probe further comprises a label group attached thereto, e.g., the label group can be a radioisotope, a fluorescent compound, an enzyme, or an enzyme co-factor. Such probes can be used as a part of a diagnostic test kit for identifying cells or tissue which misexpress a GTRAP3-18 protein or GTRAP3-18 target molecule, such as by measuring a level of a GTRAP3-18-encoding nucleic acid in a sample of cells from a subject e.g., detecting GTRAP3-18 or GTRAP3-18 target molecule mRNA levels or determining whether a genomic GTRAP3-18 or GTRAP3-18 target molecule gene has been mutated or deleted.

The methods of the invention further encompass the use of nucleic acid molecules that differ from the nucleotide sequence shown in SEQ ID NO:1 due to degeneracy of the genetic code and thus encode the same GTRAP3-18 proteins as those encoded by the nucleotide sequence shown in SEQ ID NO:1. In another embodiment, an isolated nucleic acid molecule included in the methods of the invention has a nucleotide sequence encoding a protein having an amino acid sequence shown in SEQ ID NO:2.

The methods of the invention further include the use of allelic variants of human GTRAP3-18, e.g., functional and non-functional allelic variants. Functional allelic variants are naturally occurring amino acid sequence variants of the human GTRAP3-18 protein that maintain a GTRAP3-18 activity. Functional allelic variants will typically contain only conservative substitution of one or more amino acids of SEQ ID NO:2, or substitution, deletion or insertion of non-critical residues in non-critical regions of the protein. Non-functional allelic variants are naturally occurring amino acid sequence variants of the human GTRAP3-18 protein that do not have a GTRAP3-18 activity. Non-functional allelic variants will typically contain a non-conservative substitution, deletion, or insertion or premature truncation of the amino acid sequence of SEQ ID NO:2, or a substitution, insertion or deletion in critical residues or critical regions of the protein.

The methods of the present invention may further use orthologues of the GTRAP3-18 protein. Orthologues of the GTRAP3-18 protein are proteins that are isolated from other organisms and possess the same GTRAP3-18 activity.

The methods of the present invention further include the use of nucleic acid molecules comprising the nucleotide sequence of SEQ ID NO:1, or a portion thereof, in which a mutation has been introduced. The mutation may lead to amino acid substitutions at "non-essential" amino acid residues or at "essential" amino acid residues. A "non-essential" amino acid residue is a residue that can be altered from the wild-type sequence of GTRAP3-18 (e.g., the sequence of SEQ ID NO:2) without altering the biological activity, whereas an "essential" amino acid residue is required for biological activity. For example, amino acid residues that are conserved among the GTRAP3-18 proteins from different organisms are not likely to be amenable to alteration.

Mutations can be introduced into SEQ ID NO:1 by standard techniques, such as site-directed mutagenesis and PCR-mediated mutagenesis. Preferably, conservative amino acid substitutions are made at one or more predicted non-essential amino acid residues. A "conservative amino acid substitution" is one in which the amino acid residue is replaced with an amino acid residue having a similar side chain. Families of amino acid residues having similar side chains have been defined in the art. These families include amino acids with basic side chains (e.g., lysine, arginine, histidine), acidic side chains (e.g., aspartic acid, glutamic acid), uncharged polar side chains (e.g., asparagine, glutamine, serine, threonine, tyrosine, cysteine), nonpolar side chains (e.g., glycine, alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine). Thus, a predicted nonessential amino acid residue in a GTRAP3-18 protein is preferably replaced with another amino acid residue from the same side chain family. Alternatively, in another embodiment, mutations can be introduced randomly along all or part of a GTRAP3-18 coding sequence, such as by saturation mutagenesis, and the resultant mutants can be screened for GTRAP3-18 biological activity to identify mutants that retain activity. Following mutagenesis of SEQ ID NO:1, the encoded protein can be expressed recombinantly and the activity of the protein can be determined using an assay described herein.

In other embodiments, the oligonucleotide used in the methods of the invention may include other appended groups such as peptides (e.g., for targeting host cell receptors in vivo), or agents facilitating transport across the cell membrane (see, e.g., Letsinger et al. (1989) Proc. Natl. Acad. Sci. USA 86:6553-6556; Lemaitre et al. (1987) Proc. Natl. Acad. Sci. USA 84:648-652; PCT Publication No. WO 88/09810) or the blood-brain barrier (see, e.g., PCT Publication No. WO 89/10134). In addition, oligonucleotides can be modified with hybridization-triggered cleavage agents (See, e.g., Krol et al. (1988) Biotechniques 6:958-976) or intercalating agents (see, e.g., Zon (1988) Pharm. Res. 5:539-549). To this end, the oligonucleotide may be conjugated to another molecule (e.g., a peptide, hybridization triggered cross-linking agent, transport agent, or hybridization-triggered cleavage agent).

VI. Isolated GTRAP3-18 Proteins and GTRAP3-18 Target Molecules Used in the Methods of the Invention The methods of the invention include the use of isolated GTRAP3-18 proteins and GTRAP3-18 target molecules, and biologically active portions thereof, as well as polypeptide fragments suitable for use as immunogens to raise anti-GTRAP3-18 and anti-GTRAP3-18 target molecule antibodies. In one embodiment, native GTRAP3-18 and GTRAP3-18 target molecule proteins can be isolated from cells or tissue sources by an appropriate purification scheme using standard protein purification techniques. In another embodiment, GTRAP3-18 proteins and GTRAP3-18 target molecules are produced by recombinant DNA techniques. Alternative to recombinant expression, a GTRAP3-18 protein or polypeptide or GTRAP3-18 target molecule can be synthesized chemically using standard peptide synthesis techniques.

As used herein, a "biologically active portion" of a GTRAP3-18 protein includes a fragment of a GTRAP3-18 protein having a GTRAP3-18 activity. Biologically active portions of a GTRAP3-18 protein include peptides comprising amino acid sequences sufficiently identical to or derived from the amino acid sequence of the GTRAP3-18 protein, e.g., the amino acid sequence shown in SEQ ID NO:2, which include fewer amino acids than the full length GTRAP3-18 proteins, and exhibit at least one activity of a GTRAP3-18 protein. Typically, biologically active portions comprise a domain or motif with at least one activity of the GTRAP3-18 protein. A biologically active portion of a GTRAP3-18 protein can be a polypeptide which is, for example, 25, 50, 75, 100, 125, 150, 175, or more amino acids in length. Biologically active portions of a GTRAP3-18 protein or GTRAP3-18 target molecule can be used as targets for developing agents which modulate a GTRAP3-18 activity.

In a preferred embodiment, the GTRAP3-18 protein used in the methods of the invention has an amino acid sequence shown in SEQ ID NO:2. In other embodiments, the GTRAP3-18 protein is substantially identical to SEQ ID NO:2, and retains the functional activity of the protein of SEQ ID NO:2, yet differs in amino acid sequence due to natural allelic variation or mutagenesis, as described in detail in subsection V above. Accordingly, in another embodiment, the GTRAP3-18 protein used in the methods of the invention is a protein which comprises an amino acid sequence at least about 50%, 55%, 60%, 65%, 70%, 75%, 80%, 85%, 90%, 95%, 96%, 97%, 98%, 99%, 99.1%, 99.2%, 99.3%, 99.4%, 99.5%, 99.6%, 99.7%, 99.8%, 99.9% or more identical to SEQ ID NO:2.

To determine the percent identity of two amino acid sequences or of two nucleic acid sequences, the sequences are aligned for optimal comparison purposes (e.g., gaps can be introduced in one or both of a first and a second amino acid or nucleic acid sequence for optimal alignment and non-identical sequences can be disregarded for comparison purposes). In a preferred embodiment, the length of a reference sequence aligned for comparison purposes is at least 30%, preferably at least 40%, more preferably at least 50%, even more preferably at least 60%, and even more preferably at least 70%, 80%, or 90% of the length of the reference sequence (e.g., when aligning a second sequence to an amino acid sequence of having 100 amino acid residues, at least 30, preferably at least 40, more preferably at least 50, even more preferably at least 60, and even more preferably at least 70, 80, 90 or more amino acid residues are aligned). The amino acid residues or nucleotides at corresponding amino acid positions or nucleotide positions are then compared. When a position in the first sequence is occupied by the same amino acid residue or nucleotide as the corresponding position in the second sequence, then the molecules are identical at that position (as used herein amino acid or nucleic acid "identity" is equivalent to amino acid or nucleic acid "homology"). The percent identity between the two sequences is a function of the number of identical positions shared by the sequences, taking into account the number of gaps, and the length of each gap, which need to be introduced for optimal alignment of the two sequences.

The comparison of sequences and determination of percent identity between two sequences can be accomplished using a mathematical algorithm. In a preferred embodiment, the percent identity between two amino acid sequences is determined using the Needleman and Wunsch (J. Mol. Biol. 48:444-453 (1970)) algorithm which has been incorporated into the GAP program in the GCG software package (available online through the Genetics Computer Group), using either a Blosum 62 matrix or a PAM250 matrix, and a gap weight of 16, 14, 12, 10, 8, 6, or 4 and a length weight of 1, 2, 3, 4, 5, or 6. In yet another preferred embodiment, the percent identity between two nucleotide sequences is determined using the GAP program in the GCG software package (available online through the Genetics Computer Group), using a NWSgapdna.CMP matrix and a gap weight of 40, 50, 60, 70, or 80 and a length weight of 1, 2, 3, 4, 5, or 6. In another embodiment, the percent identity between two amino acid or nucleotide sequences is determined using the algorithm of Meyers, E. and Miller, W. (Comput. Appl. Biosci. 4:11-17 (1988)) which has been incorporated into the ALIGN program (version 2.0 or 2.0U), using a PAM120 weight residue table, a gap length penalty of 12 and a gap penalty of 4.

The methods of the invention may also use GTRAP3-18 and GTRAP3-18 target molecule chimeric or fusion proteins. As used herein, a GTRAP3-18 "chimeric protein" or "fusion protein" comprises a GTRAP3-18 polypeptide operatively linked to a non-GTRAP3-18 polypeptide. A "GTRAP3-18 polypeptide" refers to a polypeptide having an amino acid sequence corresponding to a GTRAP3-18 molecule, whereas a "non-GTRAP3-18 polypeptide" refers to a polypeptide having an amino acid sequence corresponding to a protein which is not substantially homologous to the GTRAP3-18 protein, e.g., a protein which is different from the GTRAP3-18 protein and which is derived from the same or a different organism. Within a GTRAP3-18 fusion protein the GTRAP3-18 polypeptide can correspond to all or a portion of a GTRAP3-18 protein. In a preferred embodiment, a GTRAP3-18 fusion protein comprises at least one biologically active portion of a GTRAP3-18 protein. In another preferred embodiment, a GTRAP3-18 fusion protein comprises at least two biologically active portions of a GTRAP3-18 protein. Within the fusion protein, the term "operatively linked" is intended to indicate that the GTRAP3-18 polypeptide and the non-GTRAP3-18 polypeptide are fused in-frame to each other. The non-GTRAP3-18 polypeptide can be fused to the N-terminus or C-terminus of the GTRAP3-18 polypeptide.

For example, in one embodiment, the fusion protein is a GST-GTRAP3-18 fusion protein in which the GTRAP3-18 sequences are fused to the C-terminus of the GST sequences. Such fusion proteins can facilitate the purification of recombinant GTRAP3-18.

In another embodiment, this fusion protein is a protein containing a heterologous signal sequence at its N-terminus. In certain host cells (e.g., mammalian host cells), expression and/or secretion of a protein can be increased through use of a heterologous signal sequence.

Moreover, the GTRAP3-18-fusion proteins used in the methods of the invention can be used as immunogens to produce anti-GTRAP3-18 antibodies in a subject, to purify GTRAP3-18 ligands and in screening assays to identify molecules which inhibit the interaction of GTRAP3-18 with a GTRAP3-18 target molecule.

Preferably, a chimeric or fusion protein used in the methods of the invention is produced by standard recombinant DNA techniques. For example, DNA fragments coding for the different polypeptide sequences are ligated together in-frame in accordance with conventional techniques, for example by employing blunt-ended or stagger-ended termini for ligation, restriction enzyme digestion to provide for appropriate termini, filling-in of cohesive ends as appropriate, alkaline phosphatase treatment to avoid undesirable joining, and enzymatic ligation. In another embodiment, the fusion gene can be synthesized by conventional techniques including automated DNA synthesizers. Alternatively, PCR amplification of gene fragments can be carried out using anchor primers which give rise to complementary overhangs between two consecutive gene fragments which can subsequently be annealed and reamplified to generate a chimeric gene sequence (see, for example, Current Protocols in Molecular Biology, eds. Ausubel et al., John Wiley & Sons: 1992). Moreover, many expression vectors are commercially available that already encode a fusion moiety (e.g., a GST polypeptide). A GTRAP3-18 or GTRAP3-18 target molecule-encoding nucleic acid can be cloned into such an expression vector such that the fusion moiety is linked in-frame to the GTRAP3-18 protein or GTRAP3-18 target molecule.

The present invention also pertains to the use of variants of the GTRAP3-18 proteins or GTRAP3-18 target molecules which function as either GTRAP3-18 agonists (mimetics) or as GTRAP3-18 antagonists. Variants of the GTRAP3-18 proteins or GTRAP3-18 target molecules can be generated by mutagenesis, e.g., discrete point mutation or truncation of a GTRAP3-18 protein or GTRAP3-18 target molecule. An agonist of the GTRAP3-18 proteins or GTRAP3-18 target molecules can retain substantially the same, or a subset, of the biological activities of the naturally occurring form of the protein. An antagonist of a protein can inhibit one or more of the activities of the naturally occurring form of the protein by, for example, competitively modulating a GTRAP3-18-mediated activity of a GTRAP3-18 protein. Thus, specific biological effects can be elicited by treatment with a variant of limited function. In one embodiment, treatment of a subject with a variant having a subset of the biological activities of the naturally occurring form of the protein has fewer side effects in a subject relative to treatment with the naturally occurring forms of the GTRAP3-18 protein or GTRAP3-18 target molecules.

In one embodiment, variants of a GTRAP3-18 protein which function as either GTRAP3-18 agonists (mimetics) or as GTRAP3-18 antagonists can be identified by screening combinatorial libraries of mutants, e.g., truncation mutants, of a GTRAP3-18 protein for GTRAP3-18 protein agonist or antagonist activity. In one embodiment, a variegated library of GTRAP3-18 variants is generated by combinatorial mutagenesis at the nucleic acid level and is encoded by a variegated gene library. A variegated library of GTRAP3-18 variants can be produced by, for example, enzymatically ligating a mixture of synthetic oligonucleotides into gene sequences such that a degenerate set of potential GTRAP3-18 sequences is expressible as individual polypeptides, or alternatively, as a set of larger fusion proteins (e.g., for phage display) containing the set of GTRAP3-18 sequences therein. There are a variety of methods which can be used to produce libraries of potential GTRAP3-18 variants from a degenerate oligonucleotide sequence. Chemical synthesis of a degenerate gene sequence can be performed in an automatic DNA synthesizer, and the synthetic gene then ligated into an appropriate expression vector. Use of a degenerate set of genes allows for the provision, in one mixture, of all of the sequences encoding the desired set of potential GTRAP3-18 sequences. Methods for synthesizing degenerate oligonucleotides are known in the art (see, e.g., Narang, S. A. (1983) Tetrahedron 39:3; Itakura et al. (1984) Annu. Rev. Biochem. 53:323; Itakura et al. (1984) Science 198:1056; Ike et al. (1983) Nucleic Acids Res. 11:477).

In addition, libraries of fragments of a GTRAP3-18 protein coding sequence can be used to generate a variegated population of GTRAP3-18 fragments for screening and subsequent selection of variants of a GTRAP3-18 protein. In one embodiment, a library of coding sequence fragments can be generated by treating a double stranded PCR fragment of a GTRAP3-18 coding sequence with a nuclease under conditions wherein nicking occurs only about once per molecule, denaturing the double stranded DNA, renaturing the DNA to form double stranded DNA which can include sense/antisense pairs from different nicked products, removing single stranded portions from reformed duplexes by treatment with S1 nuclease, and ligating the resulting fragment library into an expression vector. By this method, an expression library can be derived which encodes N-terminal, C-terminal and internal fragments of various sizes of the GTRAP3-18 protein.

Several techniques are known in the art for screening gene products of combinatorial libraries made by point mutations or truncation, and for screening cDNA libraries for gene products having a selected property. Such techniques are adaptable for rapid screening of the gene libraries generated by the combinatorial mutagenesis of GTRAP3-18 proteins. The most widely used techniques, which are amenable to high through-put analysis, for screening large gene libraries typically include cloning the gene library into replicable expression vectors, transforming appropriate cells with the resulting library of vectors, and expressing the combinatorial genes under conditions in which detection of a desired activity facilitates isolation of the vector encoding the gene whose product was detected. Recursive ensemble mutagenesis (REM), a new technique which enhances the frequency of functional mutants in the libraries, can be used in combination with the screening assays to identify GTRAP3-18 variants (Arkin and Youvan (1992) Proc. Natl. Acad. Sci. USA 89:7811-7815; Delagrave et al. (1993) Prot. Eng. 6(3):327-331).

The methods of the present invention further include the use of anti-GTRAP3-18 antibodies and anti-GTRAP3-18 target molecule antibodies. An isolated GTRAP3-18 protein or target molecule, or a portion or fragment thereof, can be used as an immunogen to generate antibodies that bind GTRAP3-18 using standard techniques for polyclonal and monoclonal antibody preparation. A full-length protein can be used or, alternatively, antigenic peptide fragments of the protein can be used as immunogens. The antigenic peptide of GTRAP3-18 comprises at least 8 amino acid residues of the amino acid sequence shown in SEQ ID NO:2 and encompasses an epitope of GTRAP3-18 such that an antibody raised against the peptide forms a specific immune complex with the GTRAP3-18 protein. Preferably, the antigenic peptide comprises at least 10 amino acid residues, more preferably at least 15 amino acid residues, even more preferably at least 20 amino acid residues, and most preferably at least 30 amino acid residues.

Preferred epitopes encompassed by the antigenic peptide are regions of GTRAP3-18 that are located on the surface of the protein, e.g., hydrophilic regions, as well as regions with high antigenicity.

A GTRAP3-18 immunogen is typically used to prepare antibodies by immunizing a suitable subject (e.g., rabbit, goat, mouse, or other mammal) with the immunogen. An appropriate immunogenic preparation can contain, for example, recombinantly expressed GTRAP3-18 protein or a chemically synthesized GTRAP3-18 polypeptide. The preparation can further include an adjuvant, such as Freund's complete or incomplete adjuvant, or similar immunostimulatory agent. Immunization of a suitable subject with an immunogenic GTRAP3-18 preparation induces a polyclonal anti-GTRAP3-18 antibody response.

The term "antibody" as used herein refers to immunoglobulin molecules and immunologically active portions of immunoglobulin molecules, i.e., molecules that contain an antigen binding site which specifically binds (immunoreacts with) an antigen, such as a GTRAP3-18. Examples of immunologically active portions of immunoglobulin molecules include F(ab) and F(ab')2 fragments which can be generated by treating the antibody with an enzyme such as pepsin. The invention provides polyclonal and monoclonal antibodies that bind GTRAP3-18 molecules. The term "monoclonal antibody" or "monoclonal antibody composition", as used herein, refers to a population of antibody molecules that contain only one species of an antigen binding site capable of immunoreacting with a particular epitope of GTRAP3-18. A monoclonal antibody composition thus typically displays a single binding affinity for a particular GTRAP3-18 protein with which it immunoreacts.

Polyclonal anti-GTRAP3-18 antibodies can be prepared as described above by immunizing a suitable subject with a GTRAP3-18 immunogen. The anti-GTRAP3-18 antibody titer in the immunized subject can be monitored over time by standard techniques, such as with an enzyme linked immunosorbent assay (ELISA) using immobilized GTRAP3-18. If desired, the antibody molecules directed against GTRAP3-18 can be isolated from the mammal (e.g., from the blood) and further purified by well known techniques, such as protein A chromatography to obtain the IgG fraction. At an appropriate time after immunization, e.g., when the anti-GTRAP3-18 antibody titers are highest, antibody-producing cells can be obtained from the subject and used to prepare monoclonal antibodies by standard techniques, such as the hybridoma technique originally described by Kohler and Milstein (1975) Nature 256:495-497) (see also, Brown et al. (1981) J. Immunol. 127:539-46; Brown et al. (1980) J. Biol. Chem. 255: 4980-83; Yeh et al. (1976) Proc. Natl. Acad. Sci. USA 76:2927-31; and Yeh et al. (1982) Int. J. Cancer 29:269-75), the more recent human B cell hybridoma technique (Kozbor et al. (1983) Immunol. Today 4:72), the EBV-hybridoma technique (Cole et al. (1985) Monoclonal Antibodies and Cancer Therapy, Alan R. Liss, Inc., pp. 77-96) or trioma techniques. The technology for producing monoclonal antibody hybridomas is well known (see generally Kenneth, R. H. in Monoclonal Antibodies: A New Dimension in Biological Analyses, Plenum Publishing Corp., New York, N.Y. (1980); Lerner, E. A. (1981) Yale J. Biol. Med. 54:387-402; Gefter, M. L. et al. (1977) Somat. Cell Genet. 3:231-36). Briefly, an immortal cell line (typically a myeloma) is fused to lymphocytes (typically splenocytes) from a mammal immunized with a GTRAP3-18 immunogen as described above, and the culture supernatants of the resulting hybridoma cells are screened to identify a hybridoma producing a monoclonal antibody that binds GTRAP3-18.

Any of the many well known protocols used for fusing lymphocytes and immortalized cell lines can be applied for the purpose of generating an anti-GTRAP3-18 monoclonal antibody (see, e.g., Galfre, G. et al. (1977) Nature 266:55052; Gefter et al. (1977) supra; Lerner (1981) supra; and Kenneth (1980) supra). Moreover, the ordinarily skilled worker will appreciate that there are many variations of such methods which also would be useful. Typically, the immortal cell line (e.g., a myeloma cell line) is derived from the same mammalian species as the lymphocytes. For example, murine hybridomas can be made by fusing lymphocytes from a mouse immunized with an immunogenic preparation of the present invention with an immortalized mouse cell line. Preferred immortal cell lines are mouse myeloma cell lines that are sensitive to culture medium containing hypoxanthine, aminopterin and thymidine ("HAT medium"). Any of a number of myeloma cell lines can be used as a fusion partner according to standard techniques, e.g., the P3-NS1/1-Ag4-1, P3-x63-Ag8.653 or Sp2/O-Ag14 myeloma lines. These myeloma lines are available from ATCC. Typically, HAT-sensitive mouse myeloma cells are fused to mouse splenocytes using polyethylene glycol ("PEG"). Hybridoma cells resulting from the fusion are then selected using HAT medium, which kills unfused and unproductively fused myeloma cells (unfused splenocytes die after several days because they are not transformed). Hybridoma cells producing a monoclonal antibody of the invention are detected by screening the hybridoma culture supernatants for antibodies that bind GTRAP3-18, e.g., using a standard ELISA assay.

Alternative to preparing monoclonal antibody-secreting hybridomas, a monoclonal anti-GTRAP3-18 antibody can be identified and isolated by screening a recombinant combinatorial immunoglobulin library (e.g., an antibody phage display library) with GTRAP3-18 to thereby isolate immunoglobulin library members that bind GTRAP3-18. Kits for generating and screening phage display libraries are commercially available (e.g., the Pharmacia Recombinant Phage Antibody System, Catalog No. 27-9400-01; and the Stratagene SurfZAP™ Phage Display Kit, Catalog No. 240612). Additionally, examples of methods and reagents particularly amenable for use in generating and screening antibody display library can be found in, for example, Ladner et al., U.S. Pat. No. 5,223,409; Kang et al., PCT International Publication No. WO 92/18619; Dower et al., PCT International Publication No. WO 91/17271; Winter et al., PCT International Publication No. WO 92/20791; Markland et al., PCT International Publication No. WO 92/15679; Breitling et al., PCT International Publication No. WO 93/01288; McCafferty et al, PCT International Publication No. WO 92/01047; Garrard et al., PCT International Publication No. WO 92/09690; Ladner et al., PCT International Publication No. WO 90/02809; Fuchs et al. (1991) Biotechnology (NY) 9:1369-1372; Hay et al. (1992) Hum. Antibod. Hybridomas 3:81-85; Huse et al. (1989) Science 246:1275-1281; Griffiths et al. (1993) EMBO J. 12:725-734; Hawkins et al. (1992) J. Mol. Biol. 226:889-896; Clackson et al. (1991) Nature 352:624-628; Gram et al. (1992) Proc. Natl. Acad. Sci. USA 89:3576-3580; Garrard et al. (1991) Biotechnology (NY) 9:1373-1377; Hoogenboom et al. (1991) Nucleic Acids Res. 19:4133-4137; Barbas et al. (1991) Proc. Natl. Acad. Sci. USA 88:7978-7982; and McCafferty et al. (1990) Nature 348:552-554.

Additionally, recombinant anti-GTRAP3-18 antibodies, such as chimeric and humanized monoclonal antibodies, comprising both human and non-human portions, which can be made using standard recombinant DNA techniques, are within the scope of the methods of the invention. Such chimeric and humanized monoclonal antibodies can be produced by recombinant DNA techniques known in the art, for example using methods described in Robinson et al., International Application No. PCT/US86/02269; Akira et al., European Patent Application No. 184,187; Taniguchi, M., European Patent Application No. 171,496; Morrison et al., European Patent Application No. 173,494; Neuberger et al., PCT International Publication No. WO 86/01533; Cabilly et al., U.S. Pat. No. 4,816,567; Cabilly et al., European Patent Application No. 125,023; Better et al. (1988) Science 240: 1041-1043; Liu et al. (1987) Proc. Natl. Acad. Sci. USA 84:3439-3443; Liu et al. (1987) J. Immunol. 139:3521-3526; Sun et al. (1987) Proc. Natl. Acad. Sci. USA 84:214-218; Nishimura et al. (1987) Cancer Res. 47:999-1005; Wood et al.

(1985) Nature 314:446-449; Shaw et al. (1988) J. Natl. Cancer Inst. 80:1553-1559; Morrison, S. L. (1985) Science 229: 1202-1207; Oi et al. (1986) BioTechniques 4:214; Winter U.S. Pat. No. 5,225,539; Jones et al. (1986) Nature 321:552-525; Verhoeyen et al (1988) Science 239:1534; and Beidler et al. (1988) J. Immunol. 141:40534060.

An anti-GTRAP3-18 antibody can be used to detect GTRAP3-18 protein (e.g., in a cellular lysate or cell supernatant) in order to evaluate the abundance and pattern of expression of the GTRAP3-18 protein. Anti-GTRAP3-18 antibodies can be used diagnostically to monitor protein levels in tissue as part of a clinical testing procedure, e.g., to, for example, determine the efficacy of a given treatment regimen. Detection can be facilitated by coupling (i.e., physically linking) the antibody to a detectable substance. Examples of detectable substances include various enzymes, prosthetic groups, fluorescent materials, luminescent materials, bioluminescent materials, and radioactive materials. Examples of suitable enzymes include horseradish peroxidase, alkaline phosphatase, .beta.-galactosidase, or acetylcholinesterase; examples of suitable prosthetic group complexes include streptavidin/biotin and avidin/biotin; examples of suitable fluorescent materials include umbelliferone, fluorescein, fluorescein isothiocyanate, rhodamine, dichlorotriazinylamine fluorescein, dansyl chloride or phycoerythrin; an example of a luminescent material includes luminol; examples of bioluminescent materials include luciferase, luciferin, and aequorin, and examples of suitable radioactive material include 125I, 131I, 35S or 3H.

This invention is further illustrated by the following examples which should not be construed as limiting. The contents of all references, patents and published patent applications cited throughout this application, as well as the sequence listing and the figures, are incorporated herein by reference.

EXAMPLES

Example 1

Modulation of Glycosylation by GTRAP3-18

Methods
Antibodies

A synthetic peptide corresponding to the C-terminal region of EAAC1, GLT-1, EAAT4, and N-terminal region of GLAST was used to generate antisera and has been characterized previously (Rothstein, J. et al. (1994) Neuron 13:713-725). The rabbit polyclonal anti-GTRAP3-18 antibodies were raised against peptide sequences from the N and C terminus of the protein sequence. The antiserum for each was affinity purified on a column prepared by coupling the BSA-Conjugated peptide to Affi-Gel 15 (Bio-Rad, Hercules, Calif.) (Harlow and Lane, 1988). Anti-HA monoclonal antibody was obtained from BAbCo.

Subcloning of EAAC1/rEAAT3 and GTRAP3-18, and Transfection of HEK-293T Cells

The eukaryotic expression vectors pcDNA3 and pRK5 were used for expression of cDNAs in the mammalian cell line HEK 293T. Full length EAAC1 cDNA was subcloned into NotI, EcoRI sites of pcDNA3 vector or into the NotI frame of myc-PRK5 to create rEAAT3-myc fusion. GTRAP3-18 was cloned in frame with an HA sequence tag into PRK5 using Sal/Not sites. The EAAT4 cDNA was subcloned into pcDNA3.1/Hygro(+) (Invitrogen) using the EcoR I restriction site. HEK 293T cells were transfected using the FuGene (Boehringer Mannheim, Ridgefield, Conn.) transfection reagent as directed by the manufacturer.

Measurement of $Na^+$-Dependent Glutamate Transport Activity

For transfection studies, HEK cells transfected with pcDNA3.1 or PRK5 were grown in a monolayer on 6-well plates in MEM supplemented with 10% fetal bovine serum and L-glutamine. Assays were conducted 48 hours after transfection using the previously described method (Davis, K. E., et al. (1998) J. Neurosci 18:2475-2485). Samples were performed in triplicate with a $Na^+$ Krebs buffer control for each using 10 µM cold glutamate and 2 µCi $^3H$ glutamate was added unless noted. The obtained values, in CPM or DPM, from the samples were subtracted from the amount of background uptake as measured in the $Na^+$ Krebs buffer controls and normalized for the level of total protein in the well, as measured by the Bradford Protein Assay (Pierce, Rockford, Ill.).

Surface Labeling Through Membrane Impermeant Biotinylation

Biotinylation was performed as described with some modifications as in Duan, S. et al ((1993) J. Neurosci 19:10193-10200). The aliquots of whole cell, intracellular supernatant, and membrane fractions were prepared for Western analysis. SOD1 or actin was used to control for total protein and to determine whether the biotinylation reagent labels proteins in the intracellular compartment. Visualized bands were analyzed using VersaDoc software (Bio-Rad).

Enzymatic De-Glycosylation

Endo H and PNGase were purchased from New England Biolabs (Beverly, Mass.). Cell lysates following biotinylation were digested at 37° C. for 12 hours with gentle shaking with 2 U/µL of each enzyme in lysis buffer. Lysis buffer consisted of 100 mM Tris pH 7.4, 150 mM NaCl, 1 mM EDTA, 1% Triton X-100, 0.1% SDS and protease inhibitor cocktail (Roche, Basel, Switzerland) with NP-40 added to 1% preceding PNGase digestion. Non-digested samples were included in the incubation as a control. The biotinylation assay was then completed as described above.

Statistics

Statistical differences were determined by Student's t test for two-group comparisons.

Results

Figure 4A:
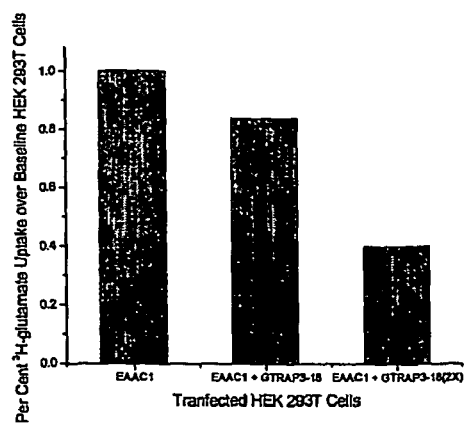
FIGS. 4A-4D depict the results of co-expression of the interacting protein, GTRAP3-18 with the neuronal transporters rEAAT3, rEAAT4, or the astrocytic transporters rEAAT1, rEAAT2, which leads to a decrease in $Na^+$-dependent L-[$^3$H]-glutamate uptake in HEK 293T cells.
Figure 4B:
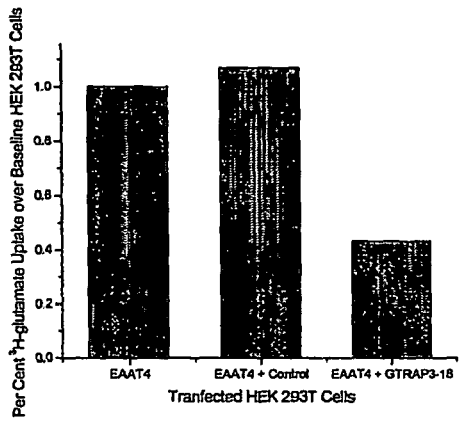
Figure 4C:
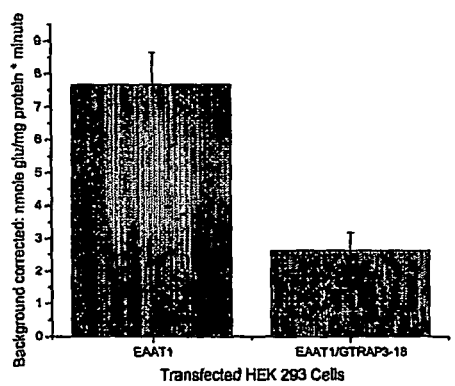
Figure 4D:
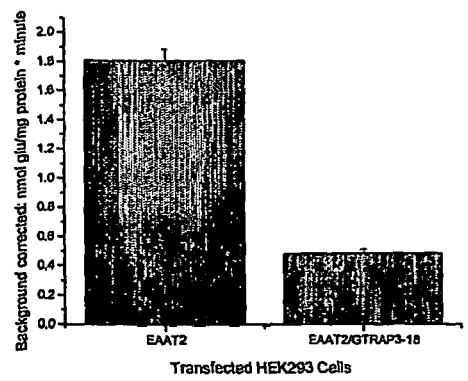

FIGS. 4A-4D show the results of co-expression of the interacting protein, GTRAP3-18 with the neuronal transporters rEAAT3, rEAAT4, or the astrocytic transporters rEAAT1, rEAAT2, which leads to a decrease in $Na^+$-dependent L-[$^3H$]-glutamate uptake in HEK 293T cells. FIGS. 4A and 4B show the results of co-transfection of rEAAT3/EAAC1 and GTRAP3-18 in HEK 293T cells at equal transfection ratio reduces EAAC1 $Na^+$-dependent L-[$^3H$]-glutamate uptake by approximately 20%, following background correction for the cell line. The decrease in transport can be brought to a higher percent of control EAAC1 expression by increasing the transfection ratios of EAAC1 to GTRAP3-18 cDNA. Co-transfection of rEAAT4 and GTRAP3-18 had a similar effect on transport. FIGS. 4C and 4D: Expansion of the analysis to the glial transporters rEAAT1 and rEAAT2 also showed a significant decrease in $Na^+$-dependent L-[$^3H$]-glutamate uptake glutamate uptake following transfection in HEK 293T cells. These transporters have a higher basal uptake activity and were measured at 40 µM total glutamate. Data are the mean±SEM of at least four independent observations and were compared by students t test (** p<0.005), and error bars are shown.

Figure 5:
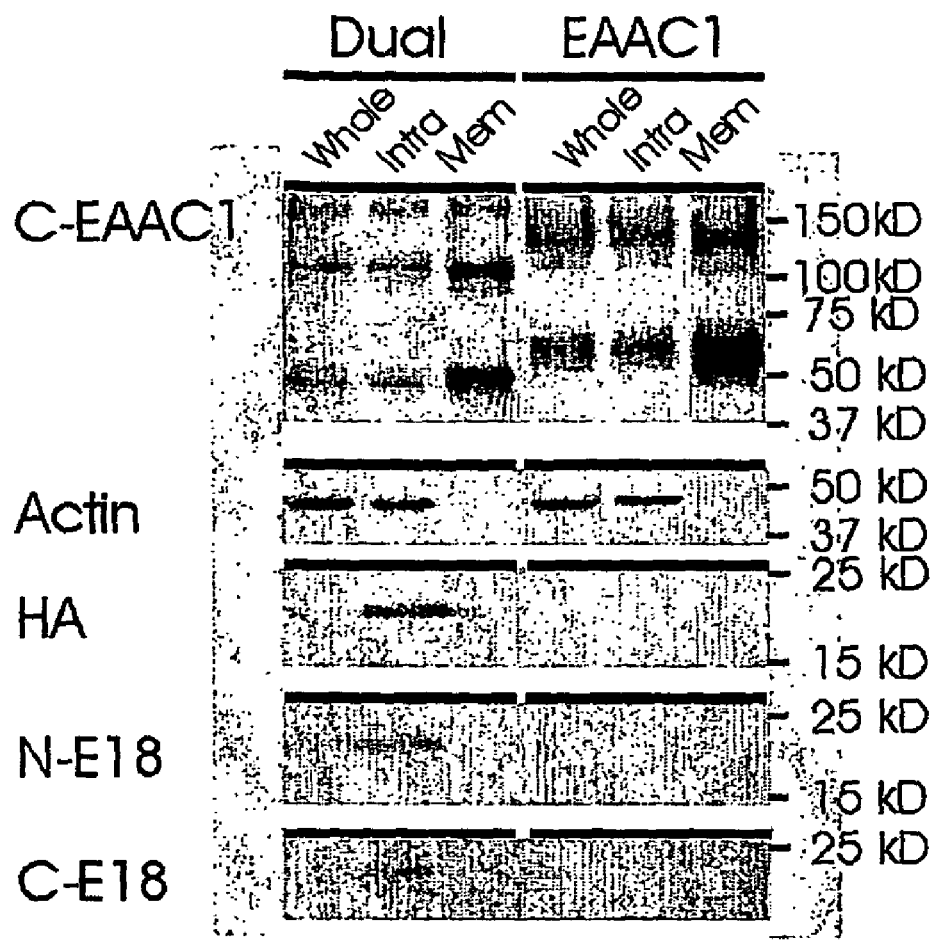
FIG. 5 depicts the results of co-expression of GTRAP3-18 with rEAAT3/EAAC1, which causes a shift in the electromobility of rEAAT3 and the other rEAATs. There is a noticeable change in the expression pattern of EAAC1 following GTRAP3-18 co-expression, seen as a 10 kD decrease in the apparent molecular following co-expression. Surface protein labeling was used to determine if this change in the electromobility pattern would also affect the cellular distribution of the transporter between the membrane surface and the intracellular trafficking compartment. Biotin was used to label the surface proteins on the HEK 293T cells and the cell lysates were purified with an avidin conjugated Sepharose column. Three lanes are shown: whole cells, the intracellular portion, and labeled membrane proteins. rEAAT3 is predominantly seen in whole cell and membrane preparations; multiple bands represent dimerization states of the transporter. The final three lanes are controls for HA-GTRAP3-18 expression.

FIG. 5 shows the results of co-expression of GTRAP3-18 with rEAAT3/EAAC1, which causes a shift in the electromobility of rEAAT3 and the other rEAATs. There is a noticeable change in the expression pattern of EAAC1 following GTRAP3-18 co-expression, seen as a 10 kD decrease in the apparent molecular following co-expression. Surface protein labeling was used to determine if this change in the electro-mobility pattern would also affect the cellular distribution of the transporter between the membrane surface and the intracellular trafficking compartment. Biotin was used to label the surface proteins on the HEK 293T cells and the cell lysates were purified with an avidin conjugated Sepharose column. Three lanes are shown: whole cells, the intracellular portion, and labeled membrane proteins. rEAAT3 is predominantly seen in whole cell and membrane preparations; multiple bands represent dimerization states of the transporter. The final three lanes are controls for HA-GTRAP3-18 expression.

Figure 6A:
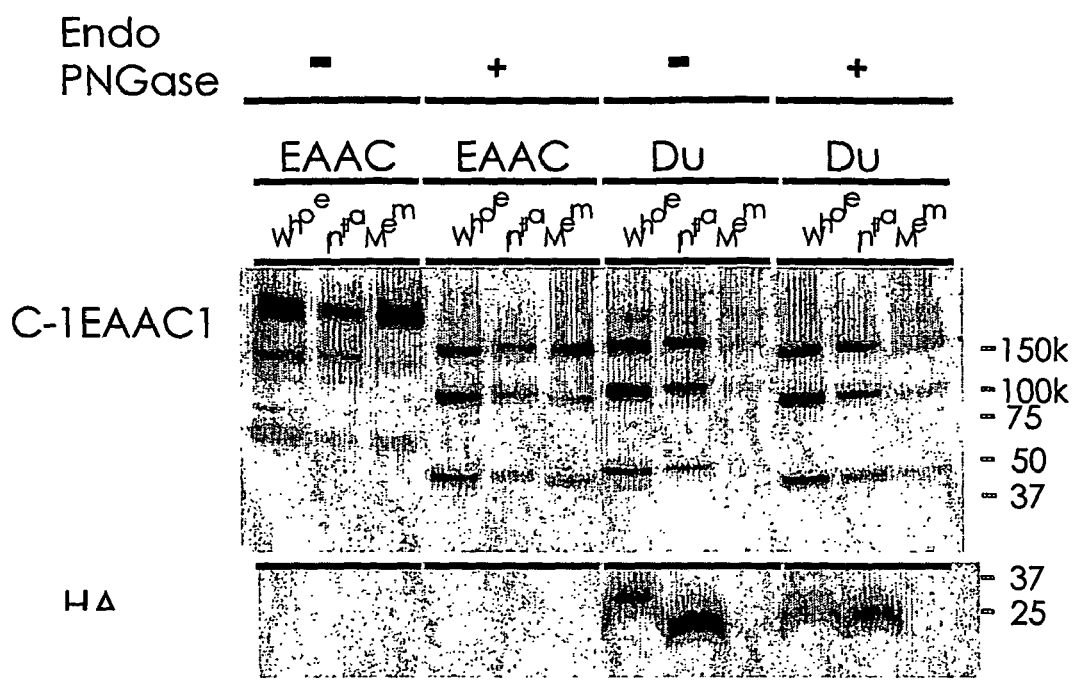
FIGS. 6A-6B depict the shift in rEAAT3/EAAC1 electromobility following co-expression with GTRAP3-18, which can be mimicked by digestion with PNGase F. This result is reproducible for tEAAT1-4.
Figure 6B:
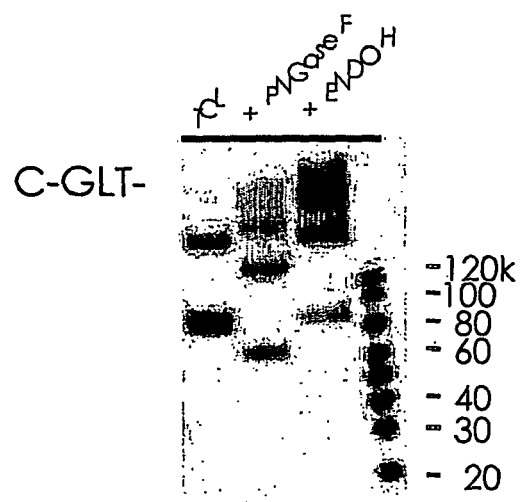

FIGS. 6A-6B depict the shift in rEAAT3/EAAC1 electro-mobility following co-expression with GTRAP3-18, which can be mimicked by digestion with PNGase F. This result is reproducible for rEAAT1-4. FIG. 6A: HEK 293T cells were transfected either with EAAC1 or EAAC1 and GTRAP3-18. The cells were harvested after 48 hours and labeled with biotin. The cell lysates were prepared as duplicate samples and incubated for 12 hours with or without the addition of the de-glycosylating enzymes PNGase F and/or Endo H. The supernatant was incubated with immobilized monomeric avidin beads to isolate biotin labeled proteins. Western blots were incubated with C-EAAC1 polyclonal and actin monoclonal antibodies as a marker for intracellular contamination of the membrane fraction. Expression of GTRAP3-18 was visualized with HA monoclonal antibody. Comparison of the effect of digestion with PNGase F and Endo H to the effect of GTRAP3-18 co-expression with EAAC1 indicates that the result is the same reproducible shift in Western immunoreactivity. Digestion of co-expressed lysates did not induce any further change in the apparent molecular weight of EAAC1. This data implicates GTRAP3-18 as a modulator of EAAC1 glycosylation. This experiment was also repeated for the other EAATs. FIG. 6B: Transporter N-linked oligosaccharides are processed to completion in the golgi to form complex oligosaccharides. Therefore, they cannot be cleaved with the high mannose specific endoglycosidase H. The molecular weight of PNGase F cleaved transporter is the same as GTRAP3-18 co-expressed transporter.

Figure 7:
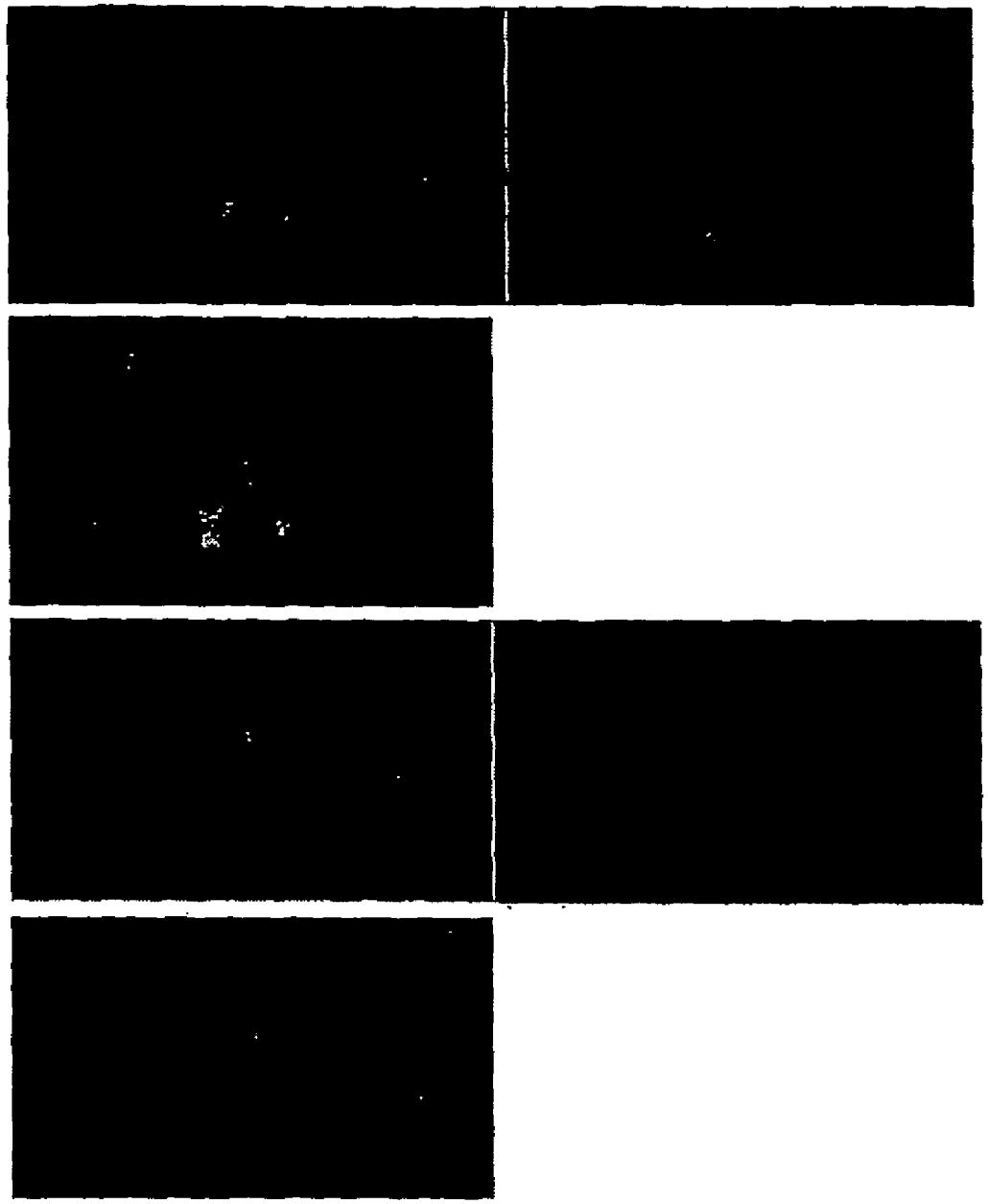
FIG. 7 depicts the localization of EAAC1 and GTRAP3-18 in HEK293 cells. EAAC1 may be seen both within the cell and expressed as puncta on the membrane surface when labeled by monoclonal myc and anti-mouse Texas Red (Vector). GTRAP3-18 appears as a reticular network throughout the cell and only co-localizes with EAAC1 that is not on the formed into puncta on the cell surface. HA-GTRAP3-18 was labeled by polyclonal HA (BAbCo) and anti-rabbit FITC (Vector). Immunofluorescence photos were taken as a stacked Z-series using a Zeiss LSM 510 confocal.

FIG. 7 depicts the localization of EAAC1 and GTRAP3-18 in HEK293 cells. EAAC1 may be seen both within the cell and expressed as puncta on the membrane surface when labeled by monoclonal myc and anti-mouse Texas Red (Vector). GTRAP3-18 appears as a reticular network throughout the cell and only co-localizes with EAAC1 that is not on the formed into puncta on the cell surface. HA-GTRAP3-18 was labeled by polyclonal HA (BAbCo) and anti-rabbit FITC (Vector). Immunofluorescence photos were taken as a stacked Z-series using a Zeiss LSM 510 confocal.

The results presented above lead to the following conclusions: GTRAP3-18 acts to modulate glycosylation of glutamate transporter proteins; GTRAP3-18 is an interacting protein of the EAAT family discovered by a yeast-two-hybrid screen; GTRAP3-18 is able to substantially reduce the activity of co-expressed rEAAT3, rEAAT4, and rEAAT1, rEAAT2 (rEAATs); GTRAP3-18 alters the apparent molecular weight of rEAATs following co-expression in HEK 293 cells. This decrease in electro-mobility is the replicated through cleavage of N-linked oligosaccharides using PNGase F; and GTRAP3-18 appears to be a reticular protein that interacts with the endoplasmic reticulum.

The invention has been described in detail with reference to preferred embodiments thereof. However, it will be appreciated that those skilled in the art, upon consideration of this disclosure, may make modification and improvements within the spirit and scope of the invention as set forth in the following claims.

What is claimed:

1. A method for identifying a compound that modulates cellular glycosylation, comprising:
   a) contacting a cell which expresses GTRAP3-18 with a test compound; and
   b) detecting a decrease in the level of glycosylation of a GTRAP3-18 target molecule, wherein the GTRAP3-18 target molecule is glutamate transporter GLAST/EAAT1, wherein the decrease in the level of glycosylation indicates a decrease the expression or activity of a GTRAP3-18 nucleic acid molecule or polypeptide, thereby identifying the test compound as a compound that modulates cellular glycosylation.

2. The method of claim 1, wherein the cell is a neuronal cell.

3. The method of claim 1, wherein the cell is a mammalian cell.

4. The method of claim 1, wherein the GTRAP3-18 polypeptide comprises an amino acid sequence as set forth in SEQ ID NO:2.

5. The method of claim 1, wherein the GRTAP3-18 polypeptide is encoded by a nucleic acid sequence comprising SEQ ID NO:1.

6. The method of claim 1, wherein the decrease in the level of glycosylation is detected via a de-glycosylation assay or glutamate transport assay.

7. The method of claim 1, wherein the GTRAP3-18 target molecule is glutamate transporter GLAST/EAAT1 and further comprises any one or more of EAAT2, EAAT3 or EAAT4.

8. A method for identifying a compound that modulates cellular glycosylation, comprising:
   a) contacting a cell which expresses GTRAP3-18 with a test compound; and
   b) detecting an increase in the level of cellular glutamate uptake of a GTRAP3-18 target molecule, wherein the GTRAP3-18 target molecule is glutamate transporter GLAST/EAAT1 and further comprises any one or more of EAAT2, EAAT3 or EAAT4, wherein the increase in glutamate uptake indicates a decrease the expression or activity of a GTRAP3-18 nucleic acid molecule or polypeptide, thereby identifying the test compound as a compound that modulates cellular glycosylation.

* * * * *

SEQUENCE LISTING

```
<160> NUMBER OF SEQ ID NOS: 10

<210> SEQ ID NO 1
<211> LENGTH: 567
<212> TYPE: DNA
<213> ORGANISM: Rattus norvegicus

<400> SEQUENCE: 1
atggacgtga accttgcccc gctccgtgcc tgggatgatt tcttcccggg ctctgatcgt      60
ttcgcacggc cggacttcag ggatatatcc aaatggaaca accgtgtagt gagcaatctg     120
ctctattacc agaccaacta cctggtggtg gctgccatga tgatttcagt cgttgggttt     180
ctgagcccct tcaacatgat ccttggagga atcattgtgg tgctggtgtt cacggggttt     240
gtgtgggcag cacacaataa agacatcctc cgccggatga agaagcagta cccaacggcc     300
tttgtcatgg tggtcatgct agccagctac ttcctcatat ccatgtttgg gggtgtcatg     360
gtctttgtgt ttggcatcac gtttcccctta ttgttgatgt tcatccatgc atccctgaga     420
cttcgaaacc tcaagaacaa actggaaaat aaaatggagg gaataggctt gaagaaaacg     480
ccgatgggca tcatcctgga tgccttggaa cagcaggaag acagcatcaa taaatttgct     540
gactacatca gcaaagccag ggagtaa                                         567

<210> SEQ ID NO 2
<211> LENGTH: 188
<212> TYPE: PRT
<213> ORGANISM: Rattus norvegicus
```

-continued

<400> SEQUENCE: 2

```
Met Asp Val Asn Leu Ala Pro Leu Arg Ala Trp Asp Asp Phe Phe Pro
1               5                  10                  15

Gly Ser Asp Arg Phe Ala Arg Pro Asp Phe Arg Asp Ile Ser Lys Trp
            20                  25                  30

Asn Asn Arg Val Val Ser Asn Leu Leu Tyr Tyr Gln Thr Asn Tyr Leu
        35                  40                  45

Val Val Ala Ala Met Met Ile Ser Val Val Gly Phe Leu Ser Pro Phe
    50                  55                  60

Asn Met Ile Leu Gly Gly Ile Val Val Leu Val Phe Thr Gly Phe
65                  70                  75                  80

Val Trp Ala Ala His Asn Lys Asp Ile Leu Arg Arg Met Lys Lys Gln
                85                  90                  95

Tyr Pro Thr Ala Phe Val Met Val Met Leu Ala Ser Tyr Phe Leu
            100                 105                 110

Ile Ser Met Phe Gly Gly Val Met Val Phe Val Phe Gly Ile Thr Phe
        115                 120                 125

Pro Leu Leu Leu Met Phe Ile His Ala Ser Leu Arg Leu Arg Asn Leu
    130                 135                 140

Lys Asn Lys Leu Glu Asn Lys Met Glu Gly Ile Gly Leu Lys Lys Thr
145                 150                 155                 160

Pro Met Gly Ile Ile Leu Asp Ala Leu Glu Gln Gln Glu Asp Ser Ile
                165                 170                 175

Asn Lys Phe Ala Asp Tyr Ile Ser Lys Ala Arg Glu
            180                 185
```

<210> SEQ ID NO 3
<211> LENGTH: 96
<212> TYPE: PRT
<213> ORGANISM: Homo sapiens P429-End EAAT3

<400> SEQUENCE: 3

```
Pro Ala Glu Asp Val Thr Leu Ile Ile Ala Val Asp Trp Leu Leu Asp
1               5                  10                  15

Arg Phe Arg Thr Met Val Asn Val Leu Gly Asp Ala Phe Gly Thr Gly
            20                  25                  30

Ile Val Glu Lys Leu Ser Lys Lys Glu Leu Glu Gln Met Asp Val Ser
        35                  40                  45

Ser Glu Val Asn Ile Val Asn Pro Phe Ala Leu Glu Ser Thr Ile Leu
    50                  55                  60

Asp Asn Glu Asp Ser Asp Thr Lys Lys Ser Tyr Val Asn Gly Gly Phe
65                  70                  75                  80

Ala Val Asp Lys Ser Asp Thr Ile Ser Phe Thr Gln Thr Ser Gln Phe
                85                  90                  95
```

<210> SEQ ID NO 4
<211> LENGTH: 121
<212> TYPE: PRT
<213> ORGANISM: Homo sapiens P439-End EAAT5

<400> SEQUENCE: 4

```
Pro Thr Asp Asp Ile Thr Leu Ile Ile Gly Val Asp Trp Ala Leu Asp
1               5                  10                  15

Arg Phe Arg Thr Met Ile Asn Val Leu Gly Asp Ala Leu Ala Ala Gly
            20                  25                  30

Ile Met Ala His Ile Cys Arg Lys Asp Phe Ala Arg Asp Thr Gly Thr
        35                  40                  45
```

-continued

Glu Lys Leu Leu Pro Cys Glu Thr Lys Pro Val Ser Leu Gln Glu Ile
    50                  55                  60

Val Ala Ala Gln Gln Asn Gly Cys Val Lys Ser Val Ala Glu Ala Ser
65                  70                  75                  80

Glu Leu Thr Leu Gly Pro Thr Cys Pro His His Val Pro Val Gln Val
                85                  90                  95

Glu Arg Asp Glu Glu Leu Pro Ala Ala Ser Leu Asn His Cys Thr Ile
            100                 105                 110

Gln Ile Ser Glu Leu Glu Thr Asn Val
            115                 120

<210> SEQ ID NO 5
<211> LENGTH: 92
<212> TYPE: PRT
<213> ORGANISM: Homo sapiens P441-end ASCT1

<400> SEQUENCE: 5

Pro Thr His Asp Leu Pro Leu Ile Leu Ala Val Asp Trp Ile Val Asp
1               5                   10                  15

Arg Thr Thr Thr Val Val Asn Val Glu Gly Asp Ala Leu Gly Ala Gly
                20                  25                  30

Ile Leu His His Leu Asn Gln Lys Ala Thr Lys Lys Gly Glu Gln Glu
            35                  40                  45

Leu Ala Glu Val Lys Val Glu Ala Ile Pro Asn Cys Lys Ser Glu Glu
        50                  55                  60

Glu Thr Ser Pro Leu Val Thr His Gln Asn Pro Ala Gly Pro Val Ala
65                  70                  75                  80

Ser Ala Pro Glu Leu Glu Ser Lys Glu Ser Val Leu
                85                  90

<210> SEQ ID NO 6
<211> LENGTH: 93
<212> TYPE: PRT
<213> ORGANISM: Homo sapiens P448-end ASCT2

<400> SEQUENCE: 6

Pro Val Asp His Ile Ser Leu Ile Leu Ala Val Asp Trp Leu Val Asp
1               5                   10                  15

Arg Ser Cys Thr Val Leu Asn Val Glu Gly Asp Ala Leu Gly Ala Gly
                20                  25                  30

Leu Leu Gln Asn Tyr Val Asp Arg Thr Glu Ser Arg Ser Thr Glu Pro
            35                  40                  45

Glu Leu Ile Gln Val Lys Ser Glu Leu Pro Leu Asp Pro Leu Pro Val
        50                  55                  60

Pro Thr Glu Glu Gly Asn Pro Leu Leu Lys His Tyr Arg Gly Pro Ala
65                  70                  75                  80

Gly Asp Ala Thr Val Ala Ser Glu Lys Glu Ser Val Met
                85                  90

<210> SEQ ID NO 7
<211> LENGTH: 82
<212> TYPE: PRT
<213> ORGANISM: Homo sapiens P462-End EAAT1

<400> SEQUENCE: 7

Pro Thr Asp Asp Ile Thr Leu Ile Ile Ala Val Asp Trp Phe Leu Asp
1               5                   10                  15

Arg Leu Arg Thr Thr Thr Asn Val Leu Gly Asp Ser Leu Gly Ala Gly
                20                  25                  30

Ile Val Glu His Leu Ser Arg His Glu Leu Lys Asn Arg Asp Val Glu
        35                  40                  45

Met Gly Asn Ser Val Ile Glu Asn Glu Met Lys Lys Pro Tyr Gln
 50                  55                  60

Leu Ile Ala Gln Asp Asn Glu Thr Glu Lys Pro Ile Asp Ser Glu Thr
 65                  70                  75                  80

Lys Met

<210> SEQ ID NO 8
<211> LENGTH: 104
<212> TYPE: PRT
<213> ORGANISM: Rat P462-End rGlt-1b

<400> SEQUENCE: 8

Pro Thr Glu Asp Ile Ser Leu Leu Val Ala Val Asp Trp Leu Leu Asp
 1               5                  10                  15

Arg Met Arg Thr Ser Val Asn Val Val Gly Asp Ser Phe Gly Ala Gly
                20                  25                  30

Ile Val Tyr His Leu Ser Lys Ser Glu Leu Asp Thr Ile Asp Ser Gln
            35                  40                  45

His Arg Met His Glu Asp Ile Glu Met Thr Lys Thr Gln Ser Ile Tyr
 50                  55                  60

Asp Asp Thr Lys Asn His Arg Glu Ser Asn Ser Asn Gln Cys Val Asn
 65                  70                  75                  80

Ala Ala His Asn Ser Val Val Ile Asp Glu Cys Lys Val Pro Phe Pro
                85                  90                  95

Phe Leu Asp Ile Glu Thr Cys Ile
            100

<210> SEQ ID NO 9
<211> LENGTH: 115
<212> TYPE: PRT
<213> ORGANISM: Rat P462-End rGlT-1

<400> SEQUENCE: 9

Pro Thr Glu Asp Ile Ser Leu Leu Val Ala Val Asp Trp Leu Leu Asp
 1               5                  10                  15

Arg Met Arg Thr Ser Val Asn Val Val Gly Asp Ser Phe Gly Ala Gly
                20                  25                  30

Ile Val Tyr His Leu Ser Lys Ser Glu Leu Asp Thr Ile Asp Ser Gln
            35                  40                  45

His Arg Met His Glu Asp Ile Glu Met Thr Lys Thr Gln Ser Val Tyr
 50                  55                  60

Asp Asp Thr Lys Asn His Arg Glu Ser Asn Ser Asn Gln Cys Val Tyr
 65                  70                  75                  80

Ala Ala His Asn Ser Val Val Ile Asp Glu Cys Lys Val Thr Leu Ala
                85                  90                  95

Ala Asn Gly Lys Ser Ala Asp Cys Ser Val Glu Glu Glu Pro Trp Lys
            100                 105                 110

Arg Glu Lys
        115

<210> SEQ ID NO 10
<211> LENGTH: 79
<212> TYPE: PRT
<213> ORGANISM: Rat P486-End EAAT4

-continued

```
<400> SEQUENCE: 10

Pro Thr Glu Asp Ile Thr Leu Ile Ile Ala Val Asp Trp Phe Leu Asp
1               5                   10                  15

Arg Leu Arg Thr Met Thr Asn Val Leu Gly Asp Ser Ile Gly Ala Ala
            20                  25                  30

Val Ile Glu His Leu Ser Gln Arg Glu Leu Glu Leu Gln Glu Ala Glu
        35                  40                  45

Leu Thr Leu Pro Ser Leu Gly Lys Pro Tyr Lys Ser Leu Met Ala Gln
    50                  55                  60

Glu Lys Gly Ala Ser Arg Gly Arg Gly Gly Asn Glu Ser Ala Met
65                  70                  75
```